United States Patent [19]

Ao et al.

[11] Patent Number: 5,677,316

[45] Date of Patent: Oct. 14, 1997

[54] 8-METHOXY-QUINOLONECARBOXYLIC ACID DERIVATIVES

[75] Inventors: Hideki Ao; Tsuyoshi Kuroda; Kazuyuki Kawasaki; Akihiko Moriguchi; Yoshifumi Ikeda, all of Chikujo-gun; Shin-ichi Uesato, Takatsuki, all of Japan

[73] Assignee: Yoshitomi Pharmaceutical Industries, Ltd., Osaka, Japan

[21] Appl. No.: 473,357

[22] Filed: Jun. 7, 1995

[30] Foreign Application Priority Data

Mar. 16, 1993 [JP] Japan .................... 5-082721
Jun. 30, 1993 [JP] Japan .................... 5-188904

[51] Int. Cl.$^6$ .................... A01N 43/42; A61K 31/47; C07D 215/16
[52] U.S. Cl. .................... 514/312; 546/156
[58] Field of Search .................... 546/156, 242; 514/312; 548/300.7, 541, 557, 566, 568; 544/128, 141, 363; D24/100

[56] References Cited

U.S. PATENT DOCUMENTS

| | | | |
|---|---|---|---|
| 4,980,470 | 12/1990 | Masuzawa et al. | 544/363 |
| 4,997,943 | 3/1991 | Iwata et al. | 544/363 |
| 5,043,450 | 8/1991 | Masuzawa et al. | 546/156 |
| 5,073,556 | 12/1991 | Iwata et al. | 514/254 |
| 5,153,204 | 10/1992 | Petersen et al. | 546/156 |
| 5,157,117 | 10/1992 | Takagi et al. | 540/541 |
| 5,164,402 | 11/1992 | Brighty | 546/156 |
| 5,173,484 | 12/1992 | Petersen et al. | 514/187 |
| 5,258,528 | 11/1993 | Domagala et al. | 548/566 |
| 5,284,842 | 2/1994 | Petersen et al. | 514/187 |
| 5,348,961 | 9/1994 | Iwata et al. | 514/312 |
| 5,359,088 | 10/1994 | Chu et al. | 548/557 |
| 5,407,932 | 4/1995 | Kuramoto et al. | 546/156 |
| 5,453,422 | 9/1995 | Petersen et al. | 514/187 |
| 5,461,165 | 10/1995 | Domagala et al. | 546/156 |

FOREIGN PATENT DOCUMENTS

| | | |
|---|---|---|
| 0 242 789 | 10/1987 | European Pat. Off. . |
| 394553 | 10/1990 | European Pat. Off. . |
| 401623 | 12/1990 | European Pat. Off. . |
| 0443498 A1 | 8/1991 | European Pat. Off. . |
| 3/72476 | 3/1991 | Japan . |
| 4-69388 | 3/1992 | Japan . |
| 4-211077 | 8/1992 | Japan . |
| 9013542 | 4/1990 | WIPO . |

OTHER PUBLICATIONS

CIP Abstract of JP 87-067660, Jul. 17, 1985.
Suto et al., *J. Med. Chem.*, 35(25), 4745–4750 (1992).
CIP Abstract of JP-91-136059/19, May 15, 1990.

*Primary Examiner*—Randy Galakowski
*Attorney, Agent, or Firm*—Wenderoth, Lind & Ponack

[57] ABSTRACT

8-Methoxy-quinolonecarboxylic acid derivatives of the formula

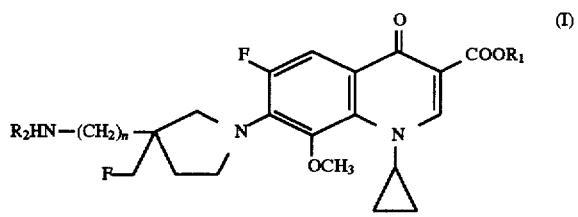

wherein $R_1$ is a hydrogen atom, a lower alkyl, a phenylalkyl or an ester residue hydrolyzable in the living body, $R_2$ is a hydrogen atom or methyl and n is an integer of 1, optical isomers thereof, pharmaceutically acceptable salts thereof and hydrates thereof. The 8-methoxy-quinolonecarboxylic acid derivatives of the present invention have enforced and a wide range of in vitro and in vivo antibacterial effects against Gram-positive bacteria, while retaining a strong antibacterial effect against Gram-negative bacteria, that the conventional quinolonecarboxylic acid antibacterial agents have. In addition, the compounds of the present invention scarcely show problematic side-effects and are low toxic. Therefore, they are expected to show superior clinical effects as antibacterial agents.

6 Claims, No Drawings

8-METHOXY-QUINOLONECARBOXYLIC ACID DERIVATIVES

TECHNICAL FIELD

The present invention relates to novel quinolonecarboxylic acid derivatives. More particularly, the present invention relates to novel 8-methoxy-quinolonecarboxylic acid derivatives having various properties to sufficiently satisfy various criteria that an antibacterial agent is requested to meet, such as extremely superior antibacterial activity, safety and so on, optical isomers thereof, pharmaceutically acceptable salts thereof and hydrates thereof.

BACKGROUND ART

There have been synthesized, developed and marketed quinolonecarboxylic acid derivatives having various chemical structures. These quinolone antibacterial agents generally show a wide range of antibacterial effects against Gram-positive bacteria and Gram-negative bacteria.

A number of compounds having cyclic amino as a substituent at the 7-position of these quinolonecarboxylic acids have been already known. In addition, many attempts have been made to modify the 7-position cyclic amino with various substituents to produce more superior compounds, and, for example, a cyclic amino such as (3-aminomethyl-3-hydroxy-1-piperidinyl) group wherein the same carbon atom constituting the cyclic amino is gem-substituted by two same or different substituents (aminomethyl and hydroxy in the above example) is known.

For example, Japanese Patent Unexamined Publication No. 19583/1987 discloses a compound having a cyclic amino substituent of the formula

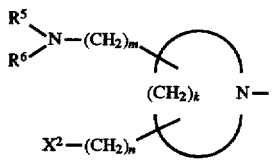

wherein each symbol is as defined in the specification of the above-mentioned Publication, at the 7-position of quinolonecarboxylic acid, and a compound having, at the 7-position, a pyrrolidinyl group gem-substituted by aminomethyl and fluoro at the 3-position, i.e. (3-aminomethyl-3-fluoro-1-pyrrolidinyl) group, is included in Examples therein. However, specific examples of the compounds having a substituent as the 7-position cyclic amino of the present invention are not included. What is more, the substituent at the 8-position is limited to a hydrogen atom or a halogen atom, and there is no disclosure or suggestion as to a lower alkoxy to be introduced as the 8-position substituent.

Japanese Patent Unexamined Publication No. 226883/1989 discloses a compound having a cyclic amino substituent of the formula

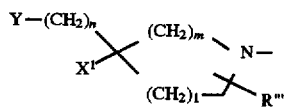

wherein each symbol is as defined in the specification of the above-mentioned Publication, at the 7-position of quinolonecarboxylic acid, and a compound having, for example, (3-hydroxy-3-methylaminomethyl-1-pyrrolidinyl) group at The 7-position is disclosed in Examples therein. Although the substituent name of (3-amino-3-fluoromethyl-1-pyrrolidinyl) group is found in examples, this is merely among the recitation of cyclic amino substituents, and the specifically exemplified compounds have a specific pyrrolidino group at the 7-position, which has hydroxy as a substituent at the 3-position thereof. What is more, the 8-position substituent is hydrogen atom, halogen atom, cyano, nitro and the like, and there is no disclosure or suggestion as to a lower alkoxy to be introduced as the 8-position substituent. Japanese Patent Unexamined Publication No. 198664/1988 discloses a compound having a cyclic amino of the formula

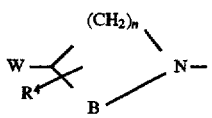

wherein each symbol is as defined in the specification of the above-mentioned Publication, at the 7-position of quinolonecarboxylic acid, and a compound having, for example, (3-aminomethyl-3-hydroxy-1-pyrrolidinyl) group is disclosed in Examples therein. The 7-position cyclic amino substituent is exemplified by (3-amino-3-methyl-1-pyrrolidinyl) group. However, this Publication does not suggest a 7-position cyclic amino substituent wherein amino or aminomethyl directly gem-substitutes the ring-constituting carbon atom, together with other substituents such as fluoromethyl. Journal of Medicinal Chemistry, vol. 35 (25), pp 4745–4750 (1992) discloses 7-(3-aminomethyl-3-methylpyrrolidin-1-yl)-1-cyclopropyl-6-fluoro-1,4-dihydro-8-methoxy-4-oxo-3-quinolinecarboxylic acid and 7-(3-amino-3-methylpyrrolidin-1-yl)-1-cyclopropyl-6-fuoro-1,4-dihydro-8-methoxy-4-oxo-3-quinolinecarboxylic acid. However, this literature does not suggest a quinolonecarboxylic acid wherein the 7-position pyrrolidino group is di-substituted by amino or aminomethyl, and fluoromethyl in a geminal form. Japanese Patent Unexamined Publication No. 124873/1990 discloses a compound having, at the 7-position of quinolonecarboxylic acid, a cyclic amino similar to the one disclosed in the aforementioned Japanese Patent Unexamined Publication No. 198664/1988 and methoxy substituted by fluorine at the 8-position. However, specific examples are 1-cyclopropyl-8-difluoromethoxy-6-fluoro-7-(3-amino-4-methoxymethylpyrrolidin-1-yl)-1,4-dihydro-4-oxoquinoline-3-carboxylic acid monohydrochloride 3/2 hydrate and so on, and the compounds having a 7-position cyclic amino which is gem-substituted are among mere recitation. In addition, there is no description that the 7-position cyclic amino is gem-substituted by fluoromethyl along with another substituent, or a description suggesting such structure. Japanese Patent Unexamined Publication No. 252772/1987 discloses a compound having methoxy at the 8-position and cyclic amino substituent at the 7-position. However, specific examples are 3-amino-4-methylpyrrolidinyl and the like, and this Publication does not suggest di-substitution of a cyclic amino such as pyrrolidino in a geminal form, with amino or aminomethyl along with fluoromethyl.

As described above, there have been heretofore synthesized, developed and used in clinical situations, various quinolone antibacterial agents. However, recent emergence of resistant bacteria showing resistance to these quinolone antibacterial agents has impaired their effectiveness. In particular, infections with methicillin-resistant Staphylococcus aureus (MRSA) has presently become a serious problem for clinical treatment. Along with the frequent use of the quinolone antibacterial agents for the treatment of such infections, quinolone resistant bacteria have appeared, thus posing new problems in that most of such bacteria are multiple drug resistant quinolone resistant MRSAs.

In the field of urinary tract infection, moreover, *Staphylococcus epidermidis* and Enterococcus, on which oral cephem preparations cannot show effects, have emerged. They have recently become resistant even to quinolone antibacterial agents, thus causing problems as causative bacteria for complicated urinary tract infection.

β-Lactam agents are scarcely effective against MRSA. Although the quinolone antibacterial agents recently developed can show effects against certain MRSA, the effects are not satisfactory. Quinolone antibacterial agents hardly show effects against quinolone resistant MRSA, *Staphylococcus epidermidis* and Enterococcus.

At present, Vancomycin and Arbekacin are clinically used as injections against such multiple drug resistant MRSA, and there is no oral preparation which can take the place of these drugs.

Accordingly, the creation of a highly safe pharmaceutical preparation showing, while retaining the antibacterial effect against Gram-negative bacteria that the conventional quinolone antibacterial agents have, a strong antibacterial effect against Gram-positive bacteria such as MRSA, quinolone resistant MRSA, *Staphylococcus epidermidis* and Enterococcus, has been a strong demand.

DISCLOSURE OF THE INVENTION

With the aim of solving the above-mentioned problems, the present inventors have substituted a cyclic amino at the 7-position of quinolonecarboxylic acid with various substituents, and found that a compound having a cyclic amino of the structure, wherein the same carbon atom on the cyclic amino is gem-substituted, shows a strong antibacterial effect, that the compound particularly shows a strong antibacterial effect when the cyclic amino is pyrrolidino, and that the compound shows particularly strong and a wide range of antibacterial effects, as well as superior safety, when the pyrrolidino is gem-substituted by fluoromethyl and aminomethyl or methylaminomethyl. Moreover, the present inventors have found that substitution of the 8-position of quinolonecarboxylic acid with methoxy markedly reduces therapeutically unfavorable effects such as phototoxicity, and increases stability of the compound structure. On the other hand, the present inventors have newly synthesized compounds having methoxy at the 8-position of quinolonecarboxylic acid and 3-amino-3-hydroxymethylpyrrolidino, 3-aminomethyl-3-hydroxymethylpyrrolidino or 3-aminomethyl-3-aminopyrrolidino at the 7-position, and confirmed that these compounds did not show the expected antibacterial effect. The present inventors have found that a specific and novel quinolone-carboxylic acid derivative wherein the same carbon atom of a pyrrolidino group constituting the 7-position substituent of quinolonecarboxylic acid is gem-substituted by two specific, different substituents (one being fluoromethyl and the other being aminomethyl or methylaminomethyl) and the 8-position is substituted by methoxy, and optical isomers thereof retain strong antibacterial effects against Gram-negative bacteria, show stronger antibacterial effects against Gram-positive bacteria, particularly strong antibacterial effects against quinolone resistant MRSA, *Staphylococcus epidermidis* and Enterococcus, than do the conventional quinolone antibacterial agents, and markedly reduce side-effects such as phototoxicity, which resulted in the completion of the invention.

That is, the present invention is detailedly as follows.

(1) 8-Methoxy-quinolonecarboxylic acid derivatives of the formula

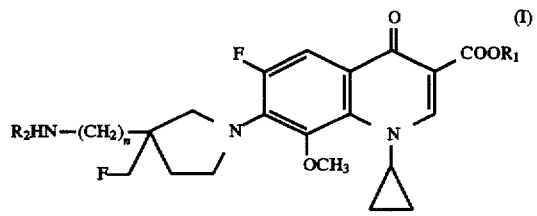

wherein $R_1$ is a hydrogen atom, a lower alkyl, a phenylalkyl or an ester residue hydrolyzable in the living body, $R_2$ is a hydrogen atom or methyl and n is an integer of 1, optical isomers thereof, pharmaceutically acceptable salts thereof and hydrates thereof [hereinafter also referred to as Compound (I)].

(2) 8-Methoxy-quinolonecarboxylic acid derivatives of the above-mentioned (1) wherein $R_1$ is a hydrogen atom, optical isomers thereof, pharmaceutically acceptable salts thereof and hydrates thereof.

(3) 8-Methoxy-quinolonecarboxylic acid derivatives of the above-mentioned (1) which are selected from 7-(3-aminomethyl-3-fluoromethylpyrrolidin-1-yl)-1-cyclopropyl-6-fluoro-1,4-dihydro-8-methoxy-4-oxo-3-quinolinecarboxylic acid and 1-cyclopropyl-6-fluoro-7-(3-fluoromethyl-3-methylaminomethylpyrrolidin-1-yl)-1,4-dihydro-8-methoxy-4-oxo-3-quinolinecarboxylic acid, optical isomers thereof, pharmaceutically acceptable salts thereof and hydrates thereof.

(4) 8-Methoxy-quinolonecarboxylic acid derivatives of the above-mentioned (1), which are selected from 7-(3-aminomethyl-3-fluoromethylpyrrolidin-1-yl)-1-cyclopropyl-6-fluoro-1,4-dihydro-8-methoxy-4-oxo-3-quinolinecarboxylic acid, (R)-7-(3-aminomethyl-3-fluoromethylpyrrolidin-1-yl)-1-cyclopropyl-6-fluoro-1,4-dihydro-8-methoxy-4-oxo-3-quinolinecarboxylic acid and (S)-7-(3-aminomethyl-3-fluoromethylpyrrolidin-1-yl)-1-cyclopropyl-6-fluoro-1,4-dihydro-8-methoxy-4-oxo-3-quinolinecarboxylic acid, optical isomers thereof, pharmaceutically acceptable salts thereof and hydrates thereof.

(5) (S)-7-(3-Aminomethyl-3-fluoromethylpyrrolidin-1-yl)-1-cyclopropyl-6-fluoro-1,4-dihydro-8-methoxy-4-oxo-3-quinolinecarboxylic acid and pharmaceutically acceptable salts thereof.

(6) Pharmaceutical compositions comprising a 8-methoxyquinolonecarboxylic acid derivative of the above-mentioned (1) to (5), an optical isomer thereof, a pharmaceutically acceptable salt thereof or a hydrate thereof, and a pharmaceutically acceptable carrier.

In the present invention, the terms used for various definitions mean the following.

Lower alkyl means straight or branched alkyl having 1 to 6, preferably 1 to 4, carbon atoms, and is exemplified by methyl, ethyl, propyl, isopropyl, butyl, sec-butyl, tert-butyl, pentyl, isopentyl, neopentyl and hexyl.

Preferred lower alkyl for $R_1$ is an alkyl having 1 to 4 carbon atoms such as methyl and ethyl.

Phenylalkyl means the above-mentioned lower alkyl substituted by a phenyl. The phenyl may be substituted by a substituent such as methyl, ethyl, methoxy, ethoxy, and the like. Examples of phenylalkyl include benzyl, phenylethyl and p-methylbenzyl, with preference given to benzyl.

Ester residue hydrolyzable in the living body is exemplified by alkanoyloxyalkyl ester such as acetoxymethyl, pivaloyloxymethyl, 1-acetoxyethyl and 1-pivaloyloxyethyl; alkoxycarbonyloxyalkyl ester such as ethoxycarbonyloxymethyl and 1-ethoxycarbonyloxyethyl; phthalidyl ester such as phthalidyl and dimethoxyphthalidyl; carbamoylalkyl ester such as carbamoylmethyl, carbamoylethyl, N-methyl carbamoylmethyl, N,N-dimethyl carbamoylmethyl and N,N-diethylcarbamoylmethyl; alkoxyalkyl ester such as methoxymethyl and methoxyethyl; aminoalkyl ester such as aminomethyl, aminoethyl and aminopropyl; alkylaminoalkyl ester such as methylaminomethyl, methylaminoethyl, methylaminopropyl, ethylaminomethyl, ethylaminoethyl, ethylaminopropyl, dimethylaminomethyl, dimethylaminoethyl, dimethylaminopropyl, diethylaminomethyl, diethylaminoethyl and diethylaminopropyl; morpholinoalkyl ester such as morpholinoethyl; piperidinoalkyl ester such as piperidinoethyl; alkylphenylamino ester such as methylphenylamino; cycloalkyloxycarbonylalkyl ester such as 1-cyclohexyloxycarbonylethyl; and 5-methyl-1,3-dioxolen-2-one-4-ylmethyl ester.

The salts of the compound (I) are exemplified by acid addition salts, metal salts and heavy metal salts. Examples of the acid addition salt include salts with inorganic acid such as hydrochloric acid, hydrobromic acid, sulfuric acid, phosphoric acid and nitric acid; salts with organic acid such as p-toluenesulfonic acid, propionic acid, succinic acid, glycolic acid, malic acid, ascorbic acid, methanesulfonic acid, citric acid, lactic acid, maleic acid, fumaric acid, acetic acid and tartaric acid. Examples of the metal salts include alkali metal salts, alkaline earth metal salts such as sodium, potassium, calcium, magnesium and aluminum salts, heavy metal salts such as copper, zinc, iron, gold, silver, platinum and manganese salts. Further, the salts are exemplified by salts with amino acid such as lysine and ornithine.

The Compounds (I) of the present invention have asymmetric carbon, and the present invention encompasses optical isomers and enantiomers derived therefrom, and racemates thereof. In addition, hydrates are also encompassed.

The Compound (I) of the present invention can be produced, for example, by the methods shown in the following.

PRODUCTION OF COMPOUND (I)

Synthesis 1

A quinolonecarboxylic acid of the formula (II)

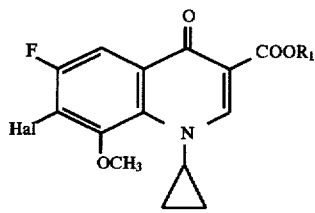

(II)

wherein $R_1$ is as defined above and Hal is a halogen atom, with particular preference given to fluorine atom, which is synthesized according to the method described in, for example, Japanese Patent Unexamined Publication No. 252772/1987, is condensed with a pyrrolidine compound of the formula (III)

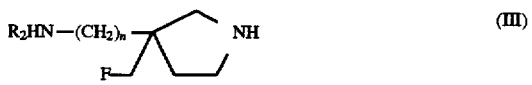

(III)

wherein each symbol is as defined above.

This condensation per se is well known and the compound (III) is used in 1 to 4-fold molar amount relative to the quinolonecarboxylic acid compound (II). The reaction proceeds without solvent or in a suitable solvent at 0°–200° C., preferably 30°–150° C., particularly preferably 30°–100° C. for 1 to 48 hours. Examples of the suitable solvent include water, alcohols such as methanol, ethanol, propanol and isopropanol, acetonitrile, pyridine, dimethylformamide, dimethyl sulfoxide, hexamethylphosphoric triamide and 1-methyl-2-pyrrolidone. In this case, an organic base such as 1,8-diazabicyclo[5.4.0]undeca-7-ene and triethylamine, or an inorganic base such as potassium carbonate, sodium carbonate, potassium hydrogencarbonate and sodium hydrogencarbonate may be used as a dehydrohalogenating agent.

Synthesis 2

A chelate compound of the formula (IV)

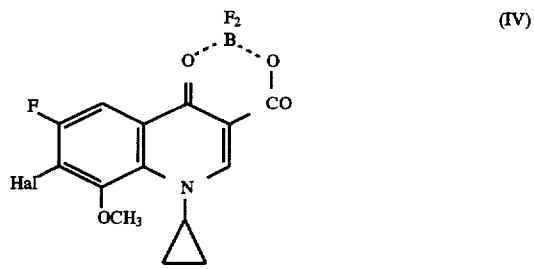

(IV)

wherein each symbol is as defined above, which is obtained by reacting the above-mentioned compound (II) with boron trifluoride, boron trifluoride complex or fluoroboric acid according to the method described in Japanese Patent Unexamined Publication No. 67290/1984, is condensed with a pyrrolidine compound of the formula (III) to give a compound of the formula

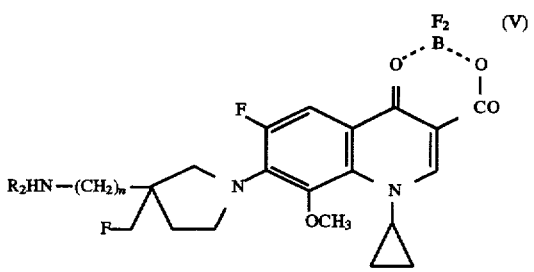

(V)

wherein each symbol is as defined above, which is further treated with a base. The carboxylic acid may be converted to a salt or an ester where necessary.

More specifically, the method described in Japanese Patent Unexamined Publication No. 67290/1984 for producing a compound (IV) from the compound (II) is carried out using an equimolar amount or more of boron trifluoride, boron trifluoride complex or fluoroboric acid relative to the compound (II), without solvent or in a suitable solvent at room temperature to 150° C., preferably 30°–100° C., particularly preferably 50°–100° C. for 1 to 48 hours.

The condensation of the compound (III) with the compound (IV) is carried out using 1 to 4-fold molar amount of the compound (III) relative to the compound (IV), without solvent or in a suitable solvent at 0°–150° C., preferably 30°–100° C. for 1 to 48 hours. Examples of the suitable solvent include water, alcohols such as methanol, ethanol, propanol and isopropanol, acetonitrile, pyridine, dimethylformamide, dimethyl sulfoxide, hexamethylphosphoric triamide and 1-methyl-2-piperidone. In this case, an organic base such as 1,8-diazabicyclo[5.4.0]undeca-7-ene and triethylamine, or an inorganic base such as potassium carbonate, sodium carbonate, potassium hydrogencarbonate and sodium hydrogencarbonate may be used as a dehydrohalogenating agent.

Examples of the base to be reacted with the compound (V) include an organic base such as 1,8-diazabicyclo[5.4.0]undeca-7-ene and triethylamine, and an inorganic base such as potassium carbonate, sodium carbonate, potassium hydrogencarbonate, sodium hydrogencarbonate, sodium hydroxide and potassium hydroxide. Examples of the suitable solvent include water, alcohols such as methanol, ethanol, propanol and isopropanol, halogenated hydrocarbon such as dichloromethane, methylene chloride and chloroform, and mixtures thereof. The reaction is carried out at room temperature to the refluxing temperature of the solvent used, for 1 to 24 hours.

It is also possible to use a boron compound of the formula

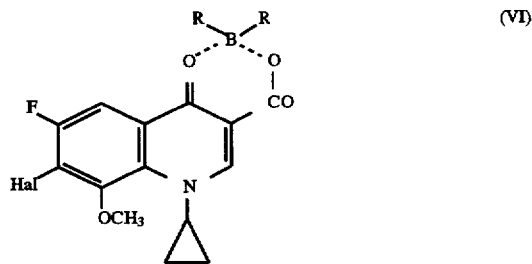
(VI)

wherein Hal is as defined above and R is aliphatic acyloxy having 2 to 6 carbon atoms, aliphatic acyloxy having 2 to 6 carbon atoms optionally substituted by halogen atom or aromatic acyloxy having 7 to 11 carbon atoms, which is obtained according to the method described in Japanese Patent Unexamined Publication No. 69388/1992, in place of the chelate compound (IV) to be used in the present synthesis.

Synthesis 3

A quinolonecarboxylic acid compound (VII) of the formula

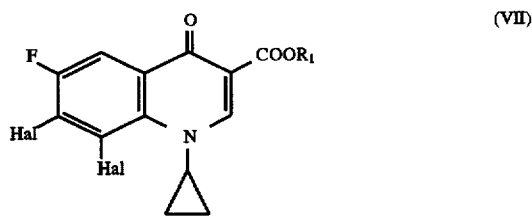
(VII)

wherein each symbol is as defined above, which is synthesized according to the method described in, for example, Japanese Patent Unexamined Publication No. 212474/1984, or a chelate compound of the formula

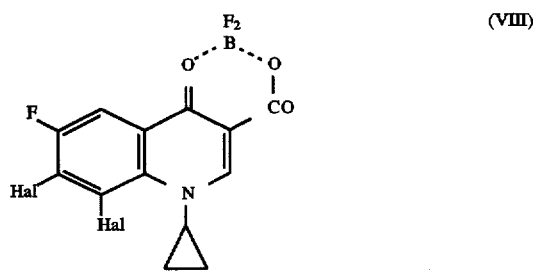
(VIII)

wherein each symbol is as defined above, which is obtained from the compound (VII) by the above-mentioned method described in Japanese Patent Unexamined Publication No. 67290/1984, is reacted with a pyrrolidine compound of the formula (III) according to the method of Synthesis 1 of Synthesis 2 to give a quinolone compound (IX) of the formula

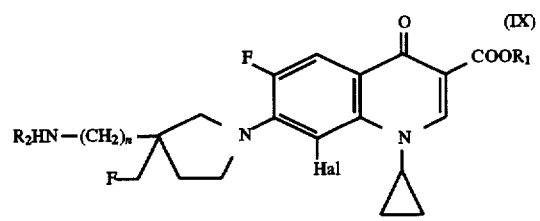
(IX)

wherein each symbol is as defined above, which is further reacted with a metal alkoxide such as sodium methoxide and potassium methoxide, whereby a compound (I) can be synthesized.

This reaction is carried out using 1 to 8-fold molar amount of the metal alkoxide such as sodium methoxide and potassium methoxide relative to the compound (IX), in a suitable solvent at 0°–200° C., preferably 30°–150° C., particularly preferably 30°100° C., for 1 to 48 hours. Examples of the suitable solvent include pyridine, dimethylformamide, dimethylacetamide, dimethyl sulfoxide, hexamethylphosphoric triamide and 1-methyl-2-piperidone.

Synthesis 4

A compound of the formula

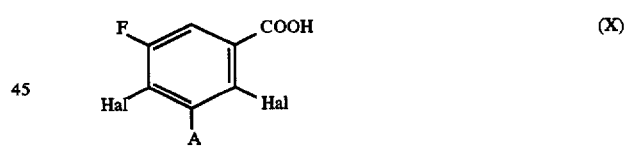
(X)

wherein Hal is as defined above and A is a halogen atom such as chlorine, fluorine and bromine or methoxy, is reacted with a cyclic amine compound (III) according to the method of Synthesis 1 to give a compound of the formula

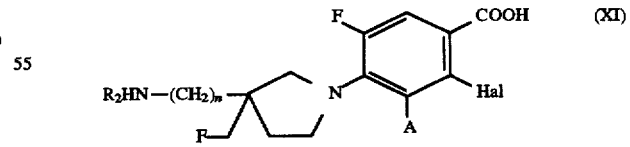
(XI)

wherein each symbol is as defined above, and the obtained compound of the formula (XI) or a reactive derivative thereof such as acid halide, thioester, acid anhydride, mixed acid anhydride, ester, acid azide and acid amide is then reacted with an aminoacrylic acid derivative of the formula

$R_3R_4NCH=CHCOOR_1$ (XII)

wherein $R_1$ is as defined above and $R_3$ and $R_4$ are the same or different and each is a lower alkyl such as methyl and ethyl. The obtained compound is reacted with a compound of the formula

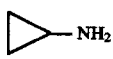 (XIII)

to give a compound of the formula

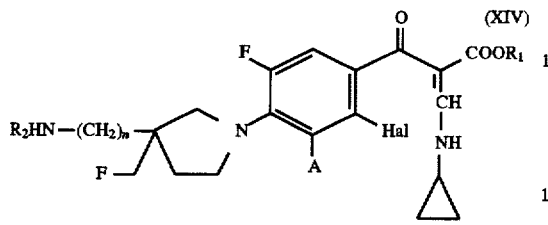 (XIV)

wherein each symbol is as defined above, which is then cyclized to give a compound of the formula

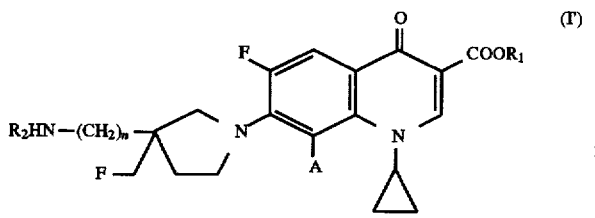 (I')

wherein each symbol is as defined above.

The reaction for obtaining a compound (XIV) from the compound (XI) is carried out using 0.8 to 3-fold molar amount of the compound (XII) and 1 to 3-fold molar amount of the compound (XIII) relative to the compound (XI) without solvent or in a suitable solvent at 0°–50° C. for the reaction with the compound (XII) and at 30°–200° C., preferably 50°–120° C., for the reaction with the compound (XIII), for 1 to 24 hours. Examples of the suitable solvent include toluene, xylene, cyclohexane, dimethylformamide and dimethyl sulfoxide. In this case, an organic base such as triethylamine, dimethylaniline and 1,8-diazabicyclo[5.4.0]undeca-7-ene or an inorganic base such as potassium carbonate, sodium carbonate, potassium hydrogencarbonate and sodium hydrogencarbonate may be used as a dehydrohalogenating agent.

The cyclization reaction is carried out by heating at 0°–200° C., preferably 50°–150° C., for 1 to several hours in an appropriate solvent such as polar solvents (e.g. dioxane, alcohol such as methanol, ethanol, propanol and butanol, dimethylformamide, dimethyl sulfoxide and sulfolane) in the presence of an appropriate basic catalyst such as potassium carbonate, sodium carbonate, 1,8-diazabicyclo[5.4.0]undeca-7-ene and potassium fluoride.

Of the compounds (I') thus obtained, a compound wherein A is a halogen atom can be converted to a compound wherein A is methoxy (the object compound of the present invention) by reacting the compound (I') with a metal alkoxide as in the aforementioned Synthesis 3.

Synthesis 5

A compound of the formula

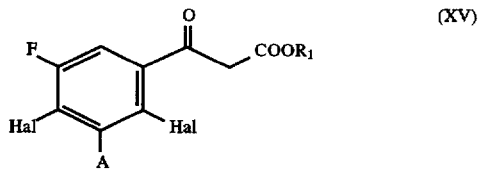 (XV)

wherein each symbol is as defined above, is reacted with a cyclic amine compound (III) according to the method of Synthesis 1 to give a compound of the formula

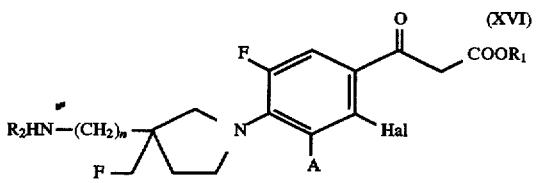 (XVI)

wherein each symbol is as defined above, which is then reacted with orthoformate-acetic anhydride or dimethylformamide dialkyl acetal (e.g. dimethylformamide dimethyl acetal and dimethylformamide diethyl acetal) and with the compound (XIII) in the same manner as in Synthesis 4 to give a compound (XIV). This compound is cyclized in the same manner as in Synthesis 4, whereby a compound (I') is obtained.

The reaction of the compound (XVI) and orthoformate or dimethylformamide dialkyl acetal is carried out using 1 to 3-fold molar amount of orthoformate or dimethylformamide dialkyl acetal relative to the compound (XVI), without solvent or in a suitable solvent at 30°–200° C., preferably 50°–150° C., for 1 to 24 hours. Examples of the suitable solvent include acetic anhydride, toluene, xylene, cyclohexane, dimethylformamide and dimethyl sulfoxide.

Of the compounds thus obtained, a compound wherein A is a halogen atom can be converted to the object compound wherein A is methoxy by reacting the compound with a metal alkoxide as in the aforementioned Synthesis 3.

Synthesis 6

When an optically active compound of the formula

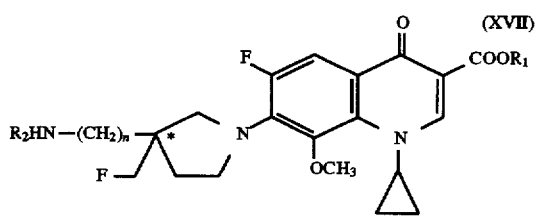 (XVII)

wherein each symbol is as defined above, is desired, a racemate of the compound of the formula (I) wherein $R_1$ is a lower alkyl or a phenylalkyl is optically resolved by a conventional method.

For optical resolution, an ester compound of the formula (I) wherein $R_1$ is a lower alkyl or a phenylalkyl, having asymmetric carbon atom, is converted to a salt with an optical active acid such as (R)-(−)-10-camphorsulfonic acid, (S)-(+)-10-camphorsulfonic acid, (R)-(−)-mandelic acid, (S)-(+)-mandelic acid, dibenzoyl-L-tartaric acid, dibenzoyl-D-tartaric acid, D-malic acid, L-malic acid, N-acetyl-L-glutamic acid, N-acetyl-D-glutamic acid, N-acetyl-L-tryptophan, N-acetyl-D-tryptophan, (R)-O-methylmandelic acid, (S)-O-methylmandelic acid, N-ortho-nitrobenzenesulfonyl-L-proline, N-ortho-nitrobenzenesulfonyl-D-proline, L-tartaric acid and D-tartaric acid, preferably with (R)-O-methylmandelic acid or (S)-O-methylmandelic acid, and the obtained salt is separated by fractional crystallization, followed by elimination of ester residue, whereby respective optical isomers are obtained.

Alternatively, an optical isomer can be obtained from a synthetic intermediate of the formula (III) which is optically resolved by a conventional method or synthesized by asymmetric synthesis, by following the above-mentioned Syntheses 1 to 5. For example, a synthetic intermediate of the formula (III) is treated with an optically active organic acid compound to form a diastereomer salt as mentioned above. The obtained diastereomer salt is subjected to fractional recrystallization and treatment with an alkali for desalting.

When the amino group of the Compounds (I) obtained in the above-mentioned Syntheses 1–6 has been protected by an amino-protecting group, wherein amino-protecting group is a protecting group conventionally used for organic synthesis and is exemplified by benzyl, substituted benzyl (e.g. 2-, 3-, or 4-chlorobenzyl, 2-, 3-, or 4-methylbenzyl, 2-, 3-, or 4-methoxybenzyl, 2-, 3-, or 4-nitrobenzyl, and 3-, 4-dimethoxybenzyl), α-methylbenzyl, (S)-α-methylbenzyl, (R)-α-methylbenzyl, diphenylmethyl, bis(4-methoxyphenyl)methyl, triphenylmethyl, phenacyl, acetyl, trifluoroacetyl, methoxycarbonyl, ethoxycarbonyl, benzyloxycarbonyl and tert-butoxycarbonyl, the protecting group can be removed by hydrogenation in an alcohol such as methanol, ethanol and propanol, water or a mixed solvent thereof in the presence of a catalyst (e.g. palladium-carbon), or by refluxing in the presence of hydrazine monohydrate and a catalyst (e.g. palladium-carbon), or by hydrolysis with an acid or alkali.

The Compound (I) of the present invention wherein $R_1$ is a lower alkyl, a phenylalkyl, or an ester residue which is hydrolyzable in the living body, is obtained by reacting a compound wherein $R_1$ is a hydrogen, with a compound of the formula $$R_1'-OH$$

wherein $R_1'$ is a group other than hydrogen atom for $R_1$, according to an esterification widely used in organic chemistry. In addition, an ester exchange reaction maybe applied.

The substituent for $R_1$ can be easily removed by hydrolysis with a conventional acid or alkali, hydrogenation in an alcohol such as methanol, ethanol and propanol, water or a mixed solvent thereof in the presence of palladium-carbon, or by refluxing using hydrazine monohydrate in the presence of palladium-carbon.

The production of the compounds of the formula (III) which are the starting materials used in the present invention is described in the following. These compounds can be produced, for example, by the following production methods.

When an optically active starting compound of the formula

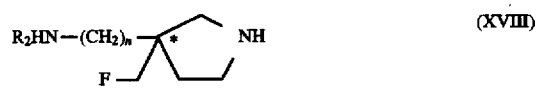

wherein each symbol is as defined above, is used, it can be synthesized by using an optically active α-methylbenzylamine by the production methods to be mentioned later.

Production of intermediate (III): Compounds of the formula (III) wherein n is 1

Production 1

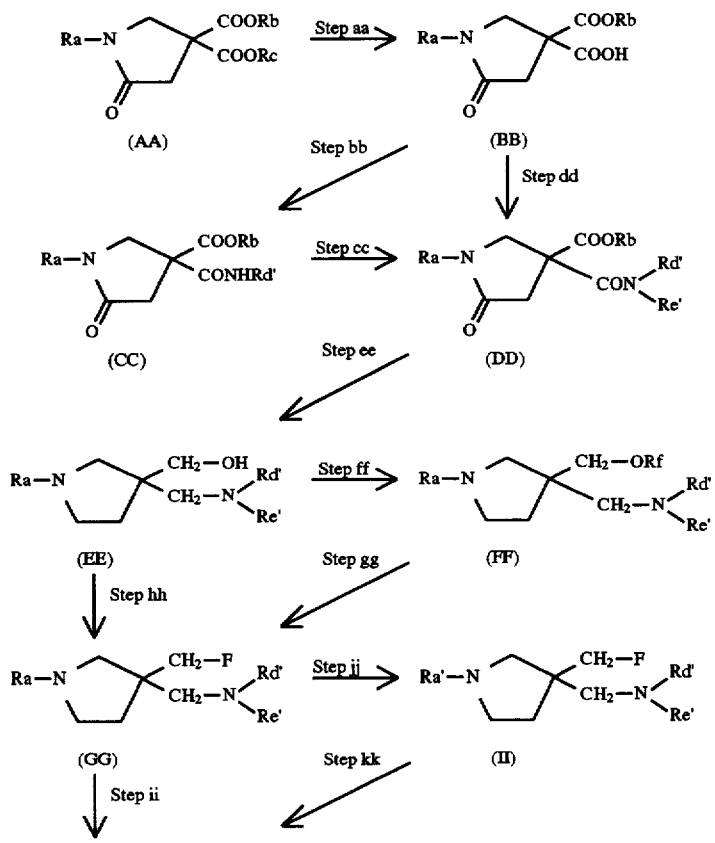

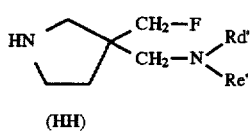

(HH)

In the above reaction steps, Ra is lower alkyl, acyl or amino-protecting group, Ra' is alkoxycarbonyl such as methoxycarbonyl and ethoxycarbonyl, Rb and Rc are each lower alkyl or phenylalkyl, Rd and Re are each lower akyl or amino-protecting group, Rd' and Re' are each hydrogen atom, lower alkyl or amino-protecting group and Rf is methanesulfonyl, trifluoromethanesulfonyl or p-toluenesulfonyl.

As used herein, acyl is an alkanoyl having 1 to 6 carbon atoms, such as formyl, acetyl, propionyl, butyryl, valeryl and pivaloyl, or arolyl such as benzoyl, toluoyl and naphthoyl.

The amino-protecting group is conventionally used for organic synthesis, and is exemplified by benzyl, substituted benzyl (e.g. 2-, 3- or 4-chlorobenzyl, 2-, 3- or 4-methylbenzyl, 2-, 3- or 4-methoxybenzyl, 2-, 3- or 4-nitrobenzyl and 3,4-dimethoxybenzyl), α-methylbenzyl, (S)-α-methylbenzyl, (R)-α-methylbenzyl, diphenylmethyl, bis(4-methoxyphenyl)methyl, triphenylmethyl, phenacyl, acetyl, trifluoroacetyl, methoxycarbonyl, ethoxycarbonyl, benzyloxycarbonyl and tert-butoxycarbonyl.

The compound (AA) which is the starting material in Production 1 can be synthesized by the method described in, for example, Japanese Patent Unexamined Publication No. 209382/1991.

Step aa

In Step aa, the compound (AA) is hydrolyzed in an alcohol such as methanol, ethanol and isopropyl alcohol, water or a mixed solvent thereof, in the presence of an inorganic acid such as lithium hydroxide, sodium hydroxide and potassium hydroxide or an acid such as hydrochloric acid and sulfuric acid to give a compound (BB).

Step bb

In Step bb, the compound (BB) is reacted with amine (Rd'NH₂) in a solvent such as alcohol (e.g. methanol, ethanol and isopropyl alcohol), tetrahydrofuran, diethyl ether, diisopropyl ether, dioxane, dimethylformamide, dimethyl sulfoxide and water, in the presence of a dehydrating agent such as dicyclohexylcarbodiimide triphenylphosphine-diethylazodicarboxylate, or the compound (BB) is converted to a halide such as acid halide or an acid anhydride and amine of Rd'NH₂ is reacted to give a compound (CC).

Step cc

In Step cc, the compound (CC) is reacted with a lower alkyl halide or phenylalkyl halide in a solvent such as alcohol (e.g. methanol, ethanol and isopropyl alcohol), tetrahydrofuran, diethyl ether, diisopropyl ether, dioxane, dimethylformamide, dimethyl sulfoxide, toluene, xylene and benzene in the presence of an inorganic base such as potassium carbonate, sodium carbonate, potassium hydrogencarbonate, sodium hydrogencarbonate, sodium methoxide, sodium ethoxide, potassium methoxide, potassium ethoxide and sodium hydride to give a compound (DD).

Step dd

In Step dd, the compound (BB) or the compound (BB) after introducing said compound into an halide such as acid chloride or an acid anhydride, is reacted with an amine (Rd'Re'NH) in the same manner as in Step bb to give a compound (DD).

Step ee

In Step ee, the compound (DD) is treated as in i) or ii) to give a compound (EE).

i) The compound (DD) is reduced with lithium aluminium hydride or sodium bis(2-methoxyethoxy)aluminum hydride in a solvent such as tetrahydrofuran, diethyl ether, diisopropyl ether, dioxane, toluene, xylene, benzene and diethylene glycol dimethyl ether to give a compound (EE).

ii) The compound (DD) is hydrolyzed under the alkaline or acidic conditions to give a carboxylic acid and reduced with diborane, sodium borohydride-iodine or sodium borohydride-sulfuric acid in a solvent such as tetrahydrofuran, diethyl ether, diisopropyl ether, dioxane, toluene, xylene, benzene and diethylene glycol dimethyl ether to give a compound (EE).

Step ff

In Step ff, the compound (EE) is reacted with p-toluenesulfonyl chloride, methanesulfonyl chloride or trifluoromethanesulfonic anhydride in a solvent such as tetrahydrofuran, diethyl ether, diisopropyl ether, toluene, xylene, dioxane, benzene, dimethylformamide, dimethylacetamide, dimethyl sulfoxide, hexane, dichloromethane, dichloroethane and chloroform in the presence of a base (e.g. pyridine and triethylamine) to give a compound (FF).

Step gg

In Step gg, the compound (FF) is reacted with a fluorinating agent such as sodium fluoride, potassium fluoride, magnesium fluoride, calcium fluoride and tetrabutylammonium fluoride in a solvent such as alcohol (e.g. methanol, ethanol and isopropyl alcohol), tetrahydrofuran, diethyl ether, diisopropyl ether, toluene, acetone, acetonitrile, dioxane, dimethylformamide, dimethylacetamide, dimethyl sulfoxide, hexane, dichloromethane, dichloroethane, chloroform, water or a mixed solvent thereof to give a compound (GG).

Step hh

In Step hh, the compound (EE) is reacted with a fluorinating agent such as diethylaminosulfur trifluoride or hexafluoropropene diethylamine, in a solvent such as tetrahydrofuran, diethyl ether, diisopropyl ether, toluene, xylene, dioxane, benzene, dimethylformamide, dimethylacetamide, dimethyl sulfoxide, hexane, chloroform, dichloromethane and dichloroethane to give a compound (GG).

Step ii

In Step ii, the compound (GG) is hydrogenolyzed in an alcohol such as methanol, ethanol and isopropyl alcohol or acetic acid, in the presence of a catalyst such as palladium-carbon, palladium hydroxide-carbon and palladium black under heating and under pressurization where necessary, or refluxing under heating for deprotection in an alcohol such as methanol, ethanol, and isopropyl alcohol or acetic acid, in the presence of a catalyst such as palladium-carbon, palladium hydroxide-carbon and palladium black, using hydrazine hydrate or ammonium formate to give a compound (HH).

The compound (GG) wherein Ra is acyl can be converted to a compound (HH) under the alkaline or acidic conditions.

Step jj

In Step jj, the compound (GG) is reacted with chlorocarbonate (e.g. methyl chlorocarbonate, ethyl chlorocarbonate, isopropyl chlorocarbonate and benzyl chlorocarbonate) in a solvent such as tetrahydrofuran, diethyl ether, diisopropyl ether, toluene, xylene, benzene, dioxane, dimethylformamide, dimethylacetamide, dimethyl sulfoxide, hexane, dichloromethane, dichloroethane and chloroform to give a compound (II).

Step kk

In Step kk, the compound (II) is reacted with sodium hydroxide, potassium hydroxide and the like, or hydrochloric acid, sulfuric acid, hydrobromic acid-acetic acid and the like without solvent or in an alcohol such as methanol, ethanol, propanol and isopropanol, water or a mixed solvent thereof to give a compound (HH).

Production 1'

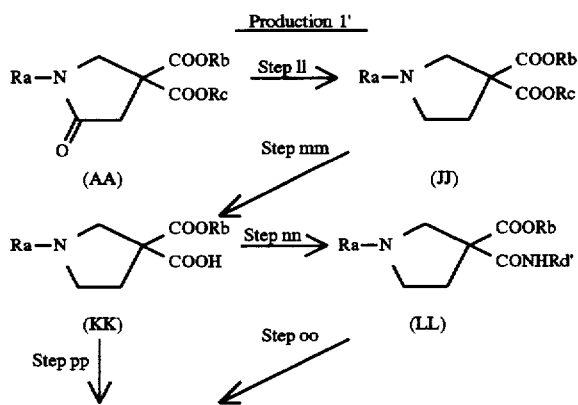

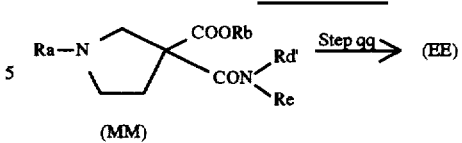

In the above reaction steps, Ra, Rb, Rc, Rd' and Re are as defined above.

Step ll

In Step ll, the compound (AA) is reduced with diborane, sodium borohydride-iodine or sodium borohydride-sulfuric acid, in a solvent such as tetrahydrofuran, diethyl ether, diisopropyl ether, toluene, xylene, benzene and diethylene glycol dimethyl ether to give a compound (JJ).

Step mm

In Step mm, the compound (JJ) is treated in the same manner as in Step aa to give a compound (KK).

Step nn

In Step nn, the compound (KK) is treated in the same manner as in Step bb to give a compound (LL).

Step oo

In Step oo, the compound (LL) is treated in the same manner as in Step cc to give a compound (MM).

Step pp

In Step pp, the Compound (KK) is treated in the same manner as in Step dd to give a compound (MM).

Step qq

In Step qq, the compound (MM) is treated in the same manner as in Step ee to give a compound (EE).

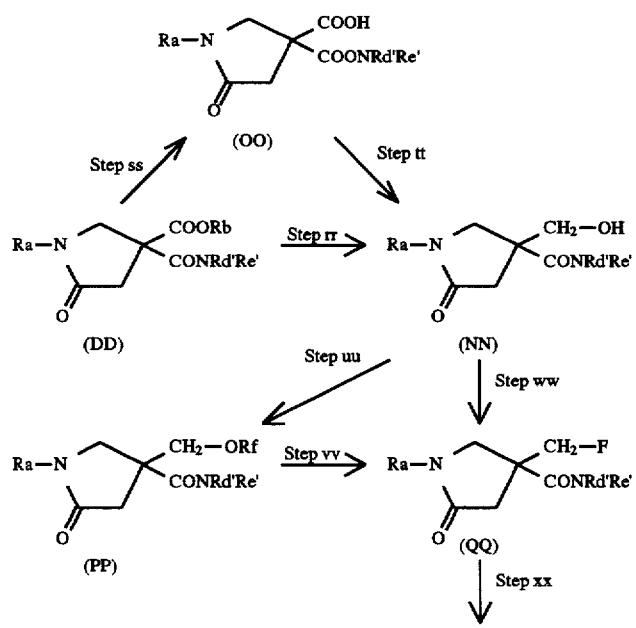

-continued
Production 2

$$Ra-N\underset{}{\overset{}{\diagup\diagdown}}\underset{CH_2-NRd'Re'}{\overset{CH_2-F}{}}$$

(GG)

In the above reaction steps, Ra, Rb, Rd', Re' and Rf are as defined above.

Step rr

In Step rr, the compound (DD) is reduced with sodium borohydride, lithium aluminum hydride and sodium bis(2-methoxyethoxy)aluminum hydride in a solvent such as alcohol (e.g. methanol, ethanol and isopropyl alcohol), tetrahydrofuran, diethyl ether, diisopropyl ether, toluene, xylene and benzene to give a compound (NN).

Step ss

In Step ss, the compound (DD) is treated in the same manner as in Production 1, Step aa to give a compound (OO).

Step tt

In Step tt, the compound (OO) is reacted with thionyl chloride, phosphorus pentachloride, phosphorus oxychloride, chlorocarbonate (e.g. methyl chlorocarbonate, ethyl chlorocarbonate and isopropyl chlorocarbonate) or dimethylformamide-oxalyl chloride in a solvent such as tetrahydrofuran, diethyl ether, diisopropyl ether, toluene, xylene, benzene, dioxane, dimethylformamide, dimethylacetamide, dimethyl sulfoxide, hexane, dichloromethane, dichloroethane and chloroform to give a reactive derivative thereof and the derivative is reduced with sodium borohydride, lithium aluminium hydride or sodium bis(2-methoxyethoxy)aluminum hydride in a solvent such as tetrahydrofuran, diethyl ether, diisopropyl ether, toluene, xylene, benzene, diethylene glycol dimethyl ether, acetonitrile, dimethylformamide and dimethylacetamide to give a compound (NN).

Step uu

In Step uu, the compound (NN) is treated in the same manner as in Production 1, Step ff to give a compound (PP).

Step vv

In Step vv, the compound (PP) is treated in the same manner as in Production 1, Step gg to give a compound (QQ).

Step ww

In Step ww, the compound (NN) is treated in the same manner as in Production 1, Step hh to give a compound (QQ).

Step xx

In Step xx, the compound (QQ) is treated in the same manner as in Production 1, Step ee, i) or the compound (QQ) is reduced with diborane, sodium borohydride-iodine or sodium borohydride-sulfuric acid to give a compound (GG).

Production 2'

Production 2'

(LL) Ra—N⟨COORb, CONHRd'⟩ —Step yy→ (RR) Ra—N⟨CH₂—OH, CONHRd'⟩

(LL) —Step zz→ (SS) Ra—N⟨CH₂—ORf, CONHRd'⟩ —Step a'a'→ (TT) Ra—N⟨CH₂—F, CONHRd'⟩

(RR) —Step b'b'→ (TT)

(TT) —Step c'c'→ (GG)

In the above reaction steps, Ra, Rb, Rd' and Rf are as defined above.

Step yy

In Step yy, the compound (LL) is treated in the same manner as in Step rr to give a compound (RR).

Step zz

In Step zz, the compound (RR) is treated in the same manner as in Production 1, Step ff to give a compound (SS).

Step a'a'

In Step a'a', the compound (SS) is treated in the same manner as in Production 1, Step gg to give a compound (TT).

Step b'b'

In Step b'b', the compound (RR) is treated in the same manner as in Production 1, Step hh to give a compound (TT).

Step c'c'

In Step c'c', the compound (TT) is treated in the same manner as in Production 1, Step cc a,d Production 2, Step xx to give a compound (GG).

Production 3

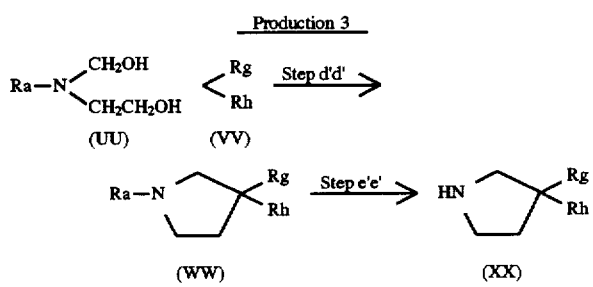

In the above reaction steps, Rg and Rh are each cyano, alkoxycarbonyl, phenylalkoxycarbonyl, carbamoyl or mono- or dialkylcarbamoyl, and Ra it as defined above.

Step d'd'

In Step d'd', the compound (UU) is reacted with the compound (VV) in a solvent such as tetrahydrofuran, diethyl ether, diisopropyl ether, toluene, xylene, benzene, acetone, acetonitrile, dioxane, dimethylformamide, dimethylacetamide, dimethyl sulfoxide, hexane, dichloromethane, dichloroethane and chloroform in the presence of triphenylphosphine-diethyl azodicarboxylate to give a compound (WW).

Step e'e'

In Step e'e', the compound (WW) is treated in the same manner as in Production 1, Step ii to give a compound (XX).

In the compound of the formula (WW) wherein Rg and Rh are each cyano, Rg and Rh can be converted to alkoxycarbonyl or phenylalkoxycarbonyl by reacting with an alcohol in the presence of an acid catalyst; to aminomethyl by reduction; to carbamoyl by hydrolysis. In the compound of the formula (WW) wherein Rg and Rh are each alkoxycarbonyl or phenylalkoxycarbonyl, Rg and Rh can be converted to hydroxymethyl by reduction; to carboxy by hydrolysis. In the compound of the formula (WW) wherein Rg and Rh are each carbamoyl, or mono- or dialkylcarbamoyl, Rg and Rh can be converted to aminomethyl and mono- or dialkylaminomethyl by reduction; to carboxy by hydrolysis. The thus-obtained compound wherein Rg and Rh are each hydroxymethyl can be introduced into a compound wherein Rg and Rh are each fluoromethyl according to Production 1, steps ff and gg or step hh and can be deprotected according to step ii.

When the compounds of the present invention have a chiral carbon atom as mentioned above, they are generally obtained as racemates. The racemates can be resolved into optically active compounds by a conventional method. Such optically active compounds can be also produced by using an optically active starting compound.

When an optically active starting compound is used, an oxo-substituted cyclic amine compound of the formula

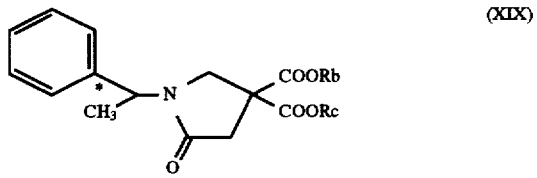

wherein each symbol is as defined above, is synthesized using an optically active α-methylbenzylamine. The obtained compound is reacted according to Production 1, Production 1', Production 2 and Production 2' for the above-mentioned synthetic starting compound. When respective synthetic intermediates have diastereomers, they can be resolved into respective diastereomers by fractional recrystallization or chromatography. The separated diastereomers are reacted according to the respective Production methods to give optically active synthetic intermediates.

In particular, when the optically active intermediate is a cyclic amine compound of the formula

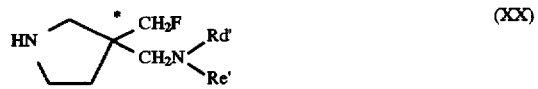

wherein Rd' and Re' are each hydrogen atom, lower alkyl or amino-protecting group, the following methods can be used for the synthesis.

Production 4

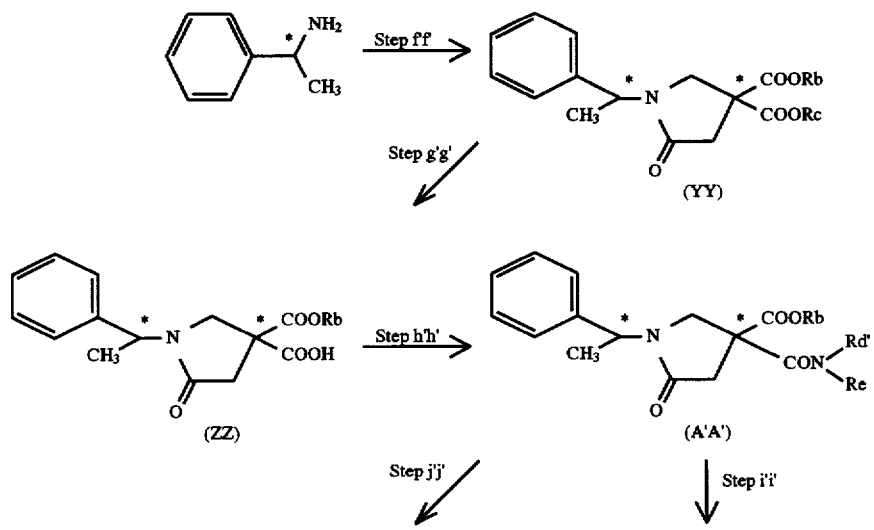

-continued
Production 4

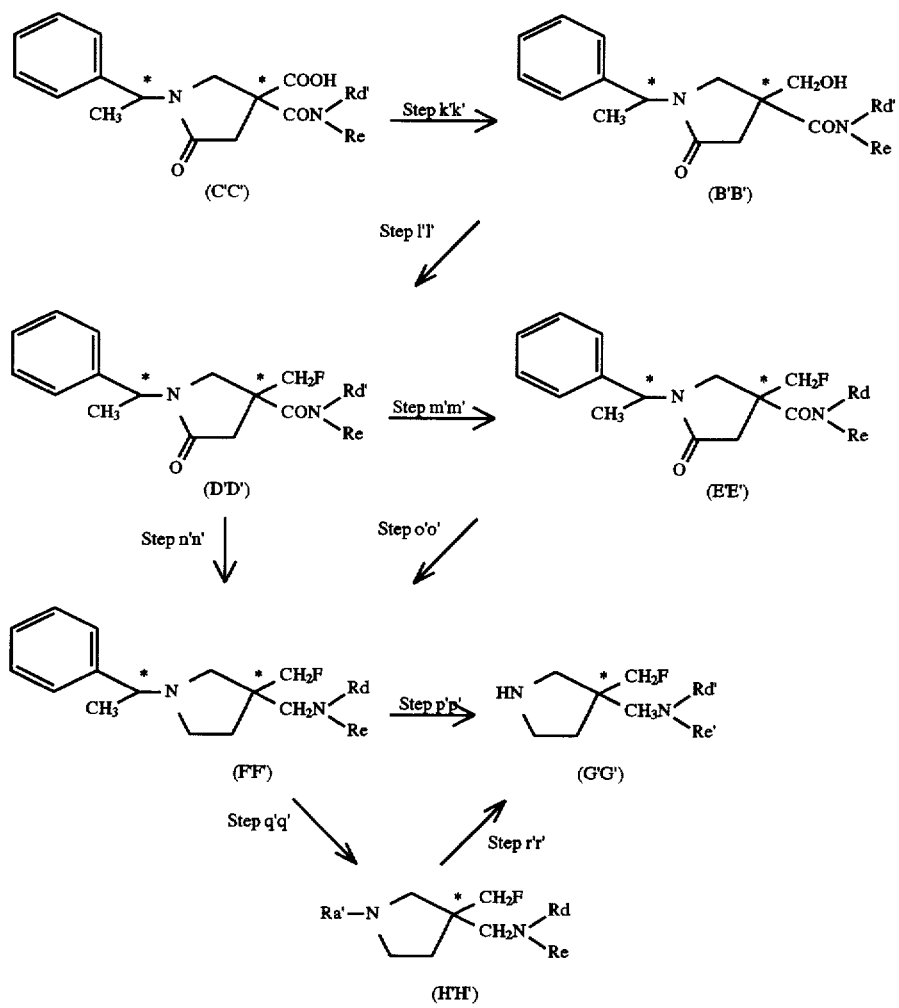

In the above reaction steps, Ra', Rb, Rc, Rd, Rd', Re and Re' are as defined above.

Step f'f'

In Step f'f', an optically active α-methylbenzylamine is reacted with formaldehyde in a solvent such as toluene, xylene and benzene in the presence of sodium hydroxide or potassium hydroxide, and the obtained compound is reacted with a compound of the formula

wherein Ri is a lower alkyl or a phenylalkyl and other symbols are as defined above, in the presence of trifluoroacetic acid to give a compound (YY).

Step g'g'

In Step g'g', the compound (YY) is treated in the same manner as in Production 1, Step aa, to give a compound (ZZ).

Step h'h'

In Step h'h', the compound (ZZ) is treated in the same manner as in Production 1, Step bb, to give a compound (A'A').

Step i'i'

In Step i'i', the compound (A'A') is treated in the same manner as in Production 2, Step rr, to give a compound (B'B').

Step j'j'

In Step j'j', the compound (A'A') is treated in the same manner as in Production 1, Step aa, to give a compound (C'C').

Step k'k'

In Step k'k', the compound (C'C') is treated in the same manner as in Production 2, Step tt, to give a compound (B'B').

Step l'l'

In Step l'l', the compound (B'B') is treated in the same manner as in Production 1, Step hh, to give a compound (D'D').

Step m'm'

In Step m'm', the compound (D'D') is treated in the same manner as in Production 1, Step cc, to give a compound (E'E').

Step n'n'

In Step n'n', the compound (D'D') is treated in the same manner as in Production 2, Step xx, to give a compound (F'F').

Step o'o'

In Step o'o', the compound (E'E') is treated in the same manner as in Production 1, Step ee, to give a compound (F'F').

Step p'p'

In Step p'p', the compound (FF') is treated in the same manner as in Production 1, Step ii, to give a compound (G'G').

Step q'q'

In Step q'q', the compound (FF') is treated in the same manner as in Production 1, Step jj, to give a compound (H'H').

Step r'r'

In Step r'r', the compound (H'H') is treated in the same manner as in Production 1, Step kk, to give a compound (G'G').

In these reaction steps, the compounds (ZZ), (A'A'), (B'B'), (C'C'), (D'D'), (E'E') and (FF') have optical isomers. These respective diastereomers are optically resolved by fractional recrystallization or chromatography, and the optically active compounds resolved are treated according to respective reaction steps mentioned above to give an optically active intermediate (G'G').

In particular, the compound (B'B') is optically resolved by silica gel column chromatography and the optically active compound obtained is preferably reacted according to the above steps.

According to the production method of the present invention, the diester compounds of (AA), (JJ) and (YY) or the ester compounds of (DD) and (A'A') are asymmetrically hydrolyzed using lipase derived from microorganism, lipoprotein lipase derived from microorganism, esterase derived from animal tissues or esterase derived from plant tissues.

While the pH of hydrolysis by an enzyme is appropriately determined according to the enzyme to be used, it is generally in the range of from 4 to 9. While the reaction temperature is appropriately determined according to the enzyme to be used, it is generally in the range of from 10° C. to 50° C.

The optically active compounds (BB), (HH), (ZZ), (OO) and (C'C') thus obtained can be reacted according to each step of respective Production methods to give an optically active compound (G'G').

The compounds (I) of the present invention thus obtained can be separated and purified from reaction mixture by recrystallization and chromatography as necessary.

The compound (I) of the present invention can be converted to pharmaceutically acceptable salts by treating with an inorganic acid (e.g. hydrochloric acid, hydrobromic acid, sulfuric acid, phosphoric acid and nitric acid), an organic acid (e.g. acetic acid, propionic acid, succinic acid, glycolic acid, lactic acid, malic acid, tartaric acid, citric acid, maleic acid, fumaric acid, methanesulfonic acid, p-toluenesulfonic acid and ascorbic acid), an amino acid (e.g. lysine and ornithine), alkali metal salts, alkaline earth metal salts (e.g. salts of sodium, potassium, magnesium and calcium) or oxide of heavy metal salts (e.g. salts of copper, zinc, iron, gold, silver, platinum and manganese), and further into hydrates or various solvates.

When the compounds of the present invention have a chiral carbon atom as mentioned above, they are generally obtained as racemates. The racemates can be resolved into optically active compounds by a conventional method. Such optically active compounds can be also produced by using an optically active starting compound. Respective enantiomers can be purified by fractional recrystallization.

When the compound of the present invention is used as an antibacterial agent, a therapeutically effective amount of the compound of the present invention is prepared using an organic or inorganic, solid or liquid pharmacologically acceptable carrier into a conventional preparation form, and administered orally, parenterally or externally.

Examples of the pharmaceutical preparation include solid preparations such as tablet, granule, powder and capsule, and liquid preparations such as suspension, syrup, emulsion and lemonade. Where necessary, auxiliary, lubricant and other conventional additives such as lactose, magnesium stearate, kaolin, sucrose, corn starch, talc, stearic acid, gelatin, agar, pectin, peanut oil and cacao butter can be added.

While the dose of the compound of the present invention varies depending on age, sex, symptom etc. of patients, the kind of disease, the kind of the compound to be administered and administration route, the compound of the present invention can be generally administered in 1 mg to about 4,000 mg or above daily. The average dose of the compound of the present invention per administration is about 50 mg, 100 mg, 250 mg, 500 mg, 1,000 mg or 2,000 mg for the treatment of the diseases caused by pathogenic microorganisms.

EXPERIMENTAL EXAMPLE

The antibacterial effect of the compound of the present invention is examined by the following test. The test compounds used are as follows.

Example 11: (S)-7-(3-aminomethyl-3-fluoromethylpyrrolidin-1-yl)-1-cyclopropyl-6-fluoro-1,4-dihydro-8-methoxy-4-oxo-3-quinolinecarboxylic acid Comparative Example 1: 9-fluoro-2,3-dihydro-3-methyl-10-(4-methyl-1-piperazinyl)-7-oxo-7H-pyrido[1,2,3-de] [1,4]benzoxazine-6-carboxylic acid (ofloxacin)

Experiment 1

Antibacterial activity (in vitro)

The in vitro antibacterial activity (minimum inhibitory concentration, MIC, μg/ml) of the test compounds was determined according to Japan Society of Chemotherapy Standard [Chemotherapy, vol. 29, pp 76–79 (1981)]. The antibacterial spectrum is shown in Table 1.

TABLE 1

| Antibacterial activity (MIC : μg/ml) | | |
|---|---|---|
| Strain | Example 11 | Comp. Ex. 1 |
| Staphylococcus aureus FDA 209P | 0.012 | 0.20 |
| S. aureus No.88[1] | 0.78 | 50 |
| S. epidermidis ATCC 12228 | 0.025 | 0.20 |
| S. epidermidis SEY-223[2] | 0.78 | >100 |
| Streptococcus pyogenes C-203* | 0.10 | 1.56 |
| S. viridans America* | 0.10 | 3.13 |
| S. pneumoniae Type-III* | 0.05 | 0.78 |
| Enterococcus faecalis LS-101 | 0.025 | 0.39 |
| E. faecalis EFY-204[2] | 1.56 | 50 |
| E. faecium EFMY-28 | 0.39 | 3.13 |
| E. faecium EFMY-207[2] | 3.13 | 100 |
| E. avium EAY-30 | 0.20 | 3.12 |
| Corynebacterium diphtheriae Tronto* | 0.025 | 0.39 |
| Escherichia coli NIHJ JC-2 | 0.10 | 0.05 |
| Shigella flexneri EW-10 | 0.025 | 0.05 |
| Klebsiella pneumoniae DT | 0.05 | 0.10 |
| Proteus vulgaris IFO 3988 | 0.78 | 0.10 |
| P. mirabilis IFO 3849 | 0.78 | 0.39 |
| Serratia marcescens IFO 12648 | 0.39 | 0.20 |
| Acinetobacter calcoaceticus ATCC 13006 | 0.10 | 0.20 |
| Citrobacter freundii IFO 12681 | 0.20 | 0.10 |
| Enterobacter cloacae IFO 12937 | 0.39 | 0.39 |
| Pseudomonas aeruginosa IFO 12582 | 1.56 | 1.56 |

Inoculated cells were $10^6$ cells/ml and the strain with * was incubated in a medium supplemented with 10% horse blood. The mark "1)" means quinolone resistant MRSA and "2)" means quinolone resistant bacteria.

incubated in a medium supplemented with 10% horse blood. The mark "1)" means quinolone resistant MRSA and "2)" means quinolone resistant bacteria.

Experimental Example 2

In the same manner as in Experimental Example 1, the antibacterial effect against specific bacteria such as Chlamydia, Mycoplasma and acid-fast bacteria and anaerobic bacteria was determined. The results are shown in Table 2.

TABLE 2

Antibacterial activity (MIC : μg/ml)

| Strain | Example 11 | Comp. Ex. 1 |
|---|---|---|
| *Mycobacterium smegmatis* IFO 3153 | 0.10 | 0.39 |
| *Mycoplasma pneumoniae* ATCC 29343 | 0.10 | 1.56 |
| *Ureaplasma urealyticum* ATCC 27618 | 0.39 | 3.13 |
| *Chlamydia trachomatis* D/UW-3Cx | 0.025 | 0.39 |
| *B. fragilis* BFY-18 | 0.20 | 1.56 |

Experimental Example 3

Protection of mice from experimental infection

Experimental infection was caused by intraperitoneal inoculation of respective bacteria to male mice. One hour after the inoculation, a test compound was orally administered to the mice. The therapeutic effect of each test compound was evaluated by reference to the 50% effective dose ($ED_{50}$) which was based on the survival ratio at 7 days after the administration according to the probit method [Proc. Soc. Exp. Med., Vol. 57, p 261–264 (1944)]. The minimum inhibitory concentration (MIC) of the infectious bacteria used was also determined. The results are shown in Table 3. The compounds of the present invention showed superior antibacterial activity in vivo.

TABLE 3

| Strain | Amount of inoculation (cells/mouse) | Test compound | MIC (μg/ml) | $ED_{50}$ (mg/mouse) (95% confidence limit) |
|---|---|---|---|---|
| *S. aureus* | 2.8 × 10$^5$ | Ex. 11 | ≦0.006 | 0.031(0.021–0.044) |
| Smith | (123 × $LD_{50}$) | Com. Ex. 1 | 0.05 | 0.208(0.137–0.344) |
| *S. aureus* | 7.5 × 10$^5$ | Ex. 11 | 0.39 | 1.540(1.103–2.151) |
| MRSA Y-238 | (185 × $LD_{50}$) | Com. Ex. 1 | >100 | >16 |
| *E. coli* | 5.0 × 10$^4$ | Ex. 11 | 0.025 | 0.011(0.008–0.015) |
| KC-14 | (744 × $LD_{50}$) | Com. Ex. 1 | 0.05 | 0.012(0.009–0.018) |

Experimental Example 4

Acute toxicity

Male ddY mice (5 per group) were orally administered with the compound of Example (2,000 mg/kg). No death case or abnormality was found.

The compound (I) of the present invention wherein n is 1 retains a strong antibacterial effect against Gram-negative bacteria, as mentioned above, and additionally shows enforced effects and a wide range of antibacterial effects against Gram-positive bacteria, both in vitro and in vivo. In addition, the problematic side-effects on the central nervous system were scarcely found and the compound was low toxic. Accordingly, clinically superior utility as an antibacterial agent is expected. In particular, the compound showed a markedly enforced antibacterial effect against Gram-positive bacteria such as *Staphylococcus aureus*, *Staphylococcus epidermidis*, *Streptococcus pneumoniae* and Enterococcus, while retaining an antibacterial effect against Gram-negative bacteria, which was equal to or superior to that of the conventional quinolonecarboxylic acid antibacterial agents. In addition, the compound showed a strong antibacterial effect against MRSA, quinolone resistant MRSA, quinolone resistant *Staphylococcus epidermidis* and quinolone resistant Enterococcus, as well as against anaerobic bacteria, Chlamydia, Mycoplasma and acid-fast bacteria. Since the strong in vitro antibacterial effect against such wide range of bacteria has been proven to be consistent with the therapeutic effect in mice, the compound is expected to show extremely superior clinical effects as a therapeutic agent for various infectious diseases caused by these pathogenic bacteria. In the absence of a suitable treatment drug for the infectious diseases caused by multiple drug resistant MRSA which poses very serious clinical problems as a causative bacterium of nosocomial infections, or the infectious diseases caused by, from among the causative bacteria of complicated urinary tract infection, *Staphylococcus epidermidis* or Enterococcus having resistance to both oral cephem preparations and quinolone preparations, the clinical utility of the compound of the present invention is considered to be extremely high. As discussed earlier, the compounds of the present invention have antibacterial effects against an extremely broad range of pathogenic bacteria including resistant bacteria. Therefore, the compounds of the present invention are expected to scarcely cause superinfection even when administered as a therapeutic agent for bacterial infections on an extended term basis to patients who acquired immune deficiency as a result of administrations of anticancer drugs and other medicaments.

EXAMPLES

The present invention is explained in the following by way of Preparative Examples and Examples. It is needless to say that the present invention is not limited to these Examples alone.

Preparative Example 1

(1) Monoethyl 1-benzyl-5-oxopyrrolidine-3,3-dicarboxylate

Diethyl 1-benzyl-5-oxopyrrolidine-3,3-dicarboxylate (61.1 g) was dissolved in ethanol (60 ml), and a solution of 85% potassium hydroxide (12.6 g) and ethanol (60 ml) was added. The mixture was allowed to stand at room temperature overnight. Ethanol was distilled away under reduced pressure and water was added. The mixture was washed with ethyl acetate. The aqueous layer was adjusted to pH 1 with hydrochloric acid and extracted with ethyl acetate. The ethyl acetate layer was washed with water, dried and concentrated to give 49.5 g of the object compound as white crystals.

(2) Ethyl 1-benzyl-3-(benzylcarbamoyl)-5-oxopyrrolidine-3-carboxylate

1-Hydroxybenztriazole (2.78 g) and dicyclohexylcarbodiimide (42.5 g) were added to a mixture of monoethyl 1-benzyl-5-oxopyrrolidine-3,3-dicarboxylate (60.0 g), benzylamine (23.2 g) and tetrahydrofuran (500 ml), and the mixture was stirred at room temperature overnight. The insoluble matter was removed by filtration and the filtrate was concentrated. Ethyl acetate (400 ml) was added and the mixture was sequentially washed with an aqueous solution of potassium carbonate, water, dilute hydrochloric acid and saturated brine, dried, and concentrated to give 78 g of the object compound as white crystals, melting point 63°–65° C.

(3) 1-Benzyl-3-(benzyluminomethyl)-3-hydroxymethylpyrrolidine

A solution of ethyl 1-benzyl-3-(benzylcarbamoyl)-5-oxopyrrolidine-3-carboxylate (9.90 g) in tetrahydrofuran (20 ml) was dropwise added to a mixture of lithium aluminum hydride (2.96 g) and tetrahydrofuran (50 ml) over 20 minutes. The mixture was refluxed for 8 hours, and water (3 ml), a 15% aqueous solution (3 ml) of sodium hydroxide and water (9 ml) were added under ice-cooling. The mixture was allowed to stand overnight. The insoluble matter was removed by filtration and the filtrate was concentrated. Ethyl acetate was added, and the mixture was washed with saturated brine, dried, and concentrated. The concentrate was purified by silica gel column chromatography to give 6.03 g of the object compound as an oil.

NMR(CDCl$_3$) δ: 1.6–1.9(m, 2H), 2.2–2.8(m, 6H), 3.56(s, 2H), 3.62(s, 2H), 3.74(s, 2H), 7.26(s, 10H).

(4) 3-Aminomethyl-3-hydroxymethylpyrrolidine

1-Benzyl-3-(benzylaminomethyl)-3-hydroxymethylpyrrolidine (2.0 g) was dissolved in ethanol (20 ml), and 10% palladium-carbon (1 g) was added. The mixture was hydrogenated under atmospheric pressure. After the completion of the reaction, the catalyst was removed, and the manure was concentrated to give the object compound as an oil.

NMR(CDCl$_3$) δ: 1.3–1.8(m, 2H), 2.6(bs, 6H), 2.8–3.0(m, 4H), 3.62(dd, 2H).

Preparative Example 2

(1) Ethyl 1-benzyl-3-(dibenzylcarbamoyl)-5-oxopyrrolidine-3-carboxylate

A solution of ethyl 1-benzyl-3-(benzylcarbamoyl)-5-oxopyrrolidine-3-carboxylate obtained in Preparative Example 1 (2) (20 g) in dimethylformamide (20 ml) was added to a mixture of 60% sodium hydride (2.5 g) and dimethylformamide (60 ml) under ice-cooling. After the mixture was stirred at room temperature for 1.5 hours, benzyl bromide (9.7 g) was added under ice-cooling and the mixture was starred for 1 hour. The reaction mixture was poured into ice water and extracted with ethyl acetate. The extract was washed with water, dried, concentrated and purified by silica gel column chromatography to give 16.3 g of the object compound as white crystals, melting point 112°–115° C.

(2) 1-Benzyl-3-(dibenzylaminomethyl)-3-hydroxymethylpyrrolidine

Ethyl 1-benzyl-3-(dibenzylcarbamoyl)-5-oxopyrrolidine-3-carboxylate (16.2 g) was treated in the same manner as in Preparative Example 1 (3) to give 11.5 g of the object compound as white crystals, melting point 65°–67° C.

(3) 1-Benzyl-3-(dibenzylaminomethyl)-3-mesyloxymethylpyrrolidine

Mesyl chloride (2.7 ml) was added to a solution of 1-benzyl-3-(dibenzylaminomethyl)-3-hydroxymethylpyrrolidine (7.88 g) and triethylamine (5.5 ml) in chloroform (80 ml) under ice-cooling, and the mixture was stirred for 30 minutes under ice-cooling. The reaction mixture was sequentially washed with an aqueous solution of sodium hydrogencarbonate and water, dried, concentrated and purified by silica gel column chromatography to give 6.97 g of the object compound as an oil.

NMR(CDCl$_3$) δ:1.5–1.9(m, 2H), 2.29(dd, 2H), 2.67(s, 2H), 2.80(s, 3H), 3.45(d, 2H), 3.60(s, 4H), 4.15(s, 2H), 7.23(s, 5H), 7.30(s, 10H).

(4) 1-Benzyl-3-(dibenzylaminomethyl)-3-fluoromethylpyrrolidine

A solution of 1-benzyl-3-(dibenzylaminomethyl)-3-mesyloxymethylpyrrolidine (6.90 g) in acetonitrile (70 ml) was added to 1N tetrabutylammonium fluoride in tetrahydrofuran (72 ml), and the mixture was starred at 40° C. for 16 hours. After concentration, the concentrate was poured into water (200 ml), and the mixture was made alkaline with aqueous ammonia and extracted with ether. The ether layer was washed with water, dried, concentrated and purified by silica gel column chromatography to give 4.37 g of the object compound as an oil.

NMR(CDCl$_3$) δ: 1.35–1.6(m, 2H), 2.05–2.6(m, 4H), 2.64 (s, 2H), 3.42(s, 2H), 3.55(s, 4H), 4.34(dd, J=48, 3 Hz, 2H), 7.22(s, 5H), 7.27(s, 10H).

(5) 3-Aminomethyl-3-fluoromethylpyrrolidine

1-Benzyl-3-(dibenzylaminomethyl)-3-fluoromethylpyrrolidine (4.55 g) was dissolved in ethanol (40 ml), and 10% palladium-carbon (1 g) and hydrazine monohydrate (2.15 g) were added. The mixture was refluxed for 1 hour. After the completion of the reaction, the catalyst was removed, and the mixture was concentrated to give the object compound as an oil.

NMR(CDCl$_3$) δ: 1.61(td, J=7, 2 Hz, 2H), 2.68(s, 3H), 2.75–2.85(m, 4H), 3.00(t, J=7 Hz, 2H), 4.38(d, J=48 Hz, 2H).

Preparative Example 3

(1) Ethyl 1-benzyl-3-(N-benzyl-N-methylcarbamoyl)-5-oxopyrrolidine-3-carboxylate Monoethyl 1-benzyl-5-oxopyrrolidine-3,3-dicarboxylate (29.1 g) obtained in Preparative Example 1 (1) and N-benzyl-N-methylamine (12.1 g) were treated in the same manner as in Preparative Example 1 (2) to give 31 g of the object compound as an oil.

NMR(CDCl$_3$) δ: 1.16(t, J=7 Hz, 3H), 2.69(s, 3H), 3.16(s, 2H), 3.59(d, J=10Hz, 1H), 4.0–4.8(m, 7H), 7.26(s, 5H), 7.29(s, 5H).

(2) 1-Benzyl-3-(N-benzyl-N-methylaminomethyl)-3-hydroxymethylpyrrolidine

Ethyl 1-benzyl-3-(N-benzyl-N-methylcarbamoyl)-5-oxopyrrolidine-3-carboxylate (19.3 g) was treated in the same manner as in Preparative Example 1 (3) to give 11.6 g of the object compound as an oil.

NMR(CDCl$_3$) δ: 1.4–1.9(m, 2H), 2.0–2.9(m, 9H), 3.50(s, 2H), 3.56(ABq, 2H), 3.58(s, 2H), 7.26(s, 10H).

(3) 3-Hydroxymethyl-3-methylaminomethylpyrrolidine

1-Benzyl-3-(N-benzyl-N-methylaminomethyl)-3-hydroxymethylpyrrolidine (6.80 g) was treated in the same manner as in Preparative Example 2 (5) to give the object compound as an oil.

NMR(CDCl$_3$) δ: 1.3–1.8(m, 2H), 2.44(s, 3H), 2.5–3.0(m, 6H), 3.25(bs, 3H), 3.59(s, 2H).

Preparative Example 4

(1) 1-Benzyl-3-(N-benzyl-N-methylaminomethyl)-3-fluoromethylpyrrolidine

A solution of mesyl chloride (3.15 ml) in methylene chloride (11 ml) was dropwise added to a solution of 1-benzyl-3-(N-benzyl-N-methylaminomethyl)-3-hydroxymethylpyrrolidine (11.0 g) obtained in Preparative Example 3 (2) and triethylamine (7.1 ml) in methylene chloride (44 ml) at not more than −20° C. After the completion of the reaction, the reaction mixture was poured into a mixture of ether (200 ml) and water (100 ml), and the ether layer was washed with water, dried and concentrated. The residue was dissolved in acetonitrile (50 ml), and the mixture was added to 1N tetrabutylammonium fluoride in tetrahydrofuran (100 ml). The mixture was stirred at 50° C. for 4 hours. After concentration, the concentrate was poured into water (300 ml), and the mixture was made alkaline with aqueous ammonia and extracted with ether. The ether layer was washed with water, dried, concentrated and purified by silica gel column chromatography to give 7.90 g of the object compound as an oil.

NMR(CDCl$_3$) δ: 1.63(td, J=7, 2 Hz, 2H), 2.21(s, 3H), 2.3–2.7(m, 6H), 3.56(s, 2H), 3.58(s, 2H), 4.41(ddd, J=48, 11, 8 Hz, 2H), 7.27(s, 10H).

(2) 3-Fluoromethyl-3-methylaminomethylpyrrolidine

1-Benzyl-3-(N-benzyl-N-methylaminomethyl)-3-fluoromethylpyrrolidine (7.90 g) was treated in the same manner as in Preparative Example 2 (5) to give the object compound as an oil.

NMR(CDCl$_3$) δ: 1.62(td, J=7, 2 Hz, 2H), 2.35(s, 2H), 2.46(s, 3H), 2.64(s, 2H), 2.8–2.9(m, 2H), 2.97(t, J=7 Hz, 2H), 4.36(d, J=48 Hz).

Preparative Example 5

(1) 1-Benzyl-2-(N,N-dibenzylcarbamoyl)-5-oxopyrrolidine-3-carboxylic acid

Monoethyl 1-benzyl-3-(N,N-dibenzylcarbamoyl)-5-oxopyrrolidine-3-carboxylate (132 g) obtained in Preparative Example 2 (1) was dissolved in methanol (900 ml), and a solution of sodium hydroxide (44.9 g) and water (450 ml) was added. The mixture was stirred at 40° C. for 4 hours and methanol was distilled away under reduced pressure. The residue was washed with toluene and hydrochloric acid was added to make the mixture acidic. The resulting mixture was extracted with ethyl acetate, and the organic layer was washed with saturated brine, dried and concentrated to quantitatively give the object compound, melting point 123°–125° C.

(2) 1-Benzyl-3-dibenzylaminomethyl-3-hydroxymethylpyrrolidine

1-Benzyl-3-(N,N-dibenzylcarbamoyl)-5-oxopyrrolidine-3-carboxylic acid (124 g) was dissolved in tetrahydrofuran (1.1 l) and sodium borohydride (79.7 g) was added over 15 minutes under ice-cooling. A solution of sulfuric acid (56 ml) in tetrahydrofuran (560 ml) was added over 1 hour under ice-cooling, and the mixture was refluxed for 3 hours. 3N Hydrochloric acid (500 ml) was added under ice-cooling and the mixture was refluxed for 2.5 hours. After concentration, water (1 l) was added and the resulting mixture was made alkaline with an aqueous solution of sodium hydroxide. The resulting mixture was extracted with ethyl acetate and washed with saturated brine. After drying, the organic layer was concentrated and purified by silica gel column chromatography to give 90 g of the object compound as white crystals, melting point 65°–67° C.

Preparative Example 6

Diethyl 1-((S)-α-methylbenzyl)-5-oxopyrrolidine-3,3-dicarboxylate

L-(−)-α-Methylbenzylamine (121 g) was dissolved in toluene (121 ml) and 37% formaldehyde (89.3 g) was dropwise added at room temperature. The mixture was stirred at 40° C. for 1 hour. Then, sodium hydroxide (1 g) and water (3 ml) were added, and the mixture was stirred for 1 hour. The reaction mixture was washed with water, and the organic layer was dried over anhydrous magnesium sulfate and concentrated under reduced pressure. Triethyl 1,1,2-ethanetricarboxylate (82 g) and trifluoroacetic acid (7.6 g) were added to the obtained oil, and the mixture was stirred at 100° C. for 24 hours. After cooling, the mixture was diluted with ethyl acetate (500 ml) and sequentially washed with 10% hydrochloric acid, water and a saturated aqueous solution of sodium hydrogencarbonate. The resulting mixture was dried over anhydrous magnesium sulfate, concentrated under reduced pressure and purified by silica gel column chromatography to give the object compound.

NMR(CDCl$_3$) δ: 1.17 (t,3H), 1.28(t,3H), 1.56(d,3H), 3.03 (dd,2H), 3.60(dd,2H), 4.12(q,2H), 4.24(q,2H), 5.48(q,2H), 7.10–7.40(m,5H).

$[α]_D$=−28.0° (c=1%, methanol).

Preparative Example 7

(RS)-3-Ethoxycarbonyl-1-((S)-α-methylbenzyl)-5-oxopyrrolidine-3-carboxylic acid

85% Potassium hydroxide (13.9 g) was dissolved in ethanol (900 ml) and diethyl 1-(S)-α-methylbenzyl)-5-oxopyrrolidine-3,3-dicarboxylate (70 g) was added. The mixture was stirred at room temperature for 4 hours. The solution was concentrated under reduced pressure, and water (500 ml) was added. The mixture was washed with toluene (300 ml), and 10% hydrochloric acid was added to the aqueous layer to make the solution acidic. The aqueous layer was extracted three times with ethyl acetate (300 ml). The extract was washed with water and saturated brine, dried over anhydrous magnesium sulfate and concentrated under reduced pressure to give the object compound, melting point 128°–135° C.

Preparative Example 8

Ethyl (RS)-3-(N,N-dibenzylcarbamoyl)-1-((S)-α-methylbenzyl)-5-oxo-pyrrolidine-3-carboxylate (RS)-3-Ethoxycarbonyl-1-((S)-α-methylbenzyl)-5-oxopyrrolidine-3-carboxylic acid (30.5 g) was dissolved in 1,2-dichloroethane (92 ml), and thionyl chloride (11 ml) and one drop of N,N-dimethylformamide were added. The mixture was refluxed for 2 hours and the reaction mixture was concentrated under reduced pressure. The obtained oil was dissolved in toluene (39 ml) and the mixture was dropwise added to a solution of dibenzylamine (23.7 g) and triethylamine (12.2 g) in toluene (130 ml) under ice-cooling. The mixture was stirred at room temperature for 3 hours. The reaction mixture was washed with water, a sodium hydrogencarbonate-10% aqueous hydrochloric acid solution and water, and dried over anhydrous magnesium sulfate to give the object compound.

Preparative Example 9

(S)-N,N-Dibenzyl-3-hydroxymethyl-1-((S)-α-methylbenzyl)-5-oxopyrrolidine-3-carboxamide and (R)-N,N-dibenzyl-3-hydroxymethyl-1-((S)-α-methylbenzyl)-5-oxopyrrolidine-3-carboxamide Ethyl (RS)-3-(N,N-dibenzylcarbamoyl)-1-((S)-α-methylbenzyl)-5-oxopyrrolidine-3-carboxylate (46 g) was dissolved in methanol (700 ml), and sodium borohydride (50 g) was portionwise added under water-cooling. The mixture was allowed to stand overnight at room temperature, and the reaction mixture was concentrated under reduced pressure. Ethyl acetate (200 ml) was added and the mixture was washed with water and dried over anhydrous magnesium sulfate. The solvent was distilled away to give a mixture of diastereomers. The mixture was separated by silica gel column chromatography using a mixed solvent of n-hexane:ethyl acetate (1:1) to give an (S)-isomer, melting point 140°–142° C., $[α]_D$=−35.0° (c=1%, methanol), and an (R)-isomer, melting point 164°–166° C., $[α]_D$=−86.9° (c=1%, methanol), respectively.

Preparative Example 10

(R)-N,N-Dibenzyl-3-fluoromethyl-1-((S)-α-methylbenzyl)-5-oxopyrrolidine-3-carboxamide (S)-N,N-Dibenzyl-3-hydroxymethyl-1-((S)-α-methylbenzyl)-5-oxopyrrolidine-3-carboxamide (7.61 g) was dissolved in chloroform (80 ml) and hexafluoropropenediethylamine (7.85 g) was added. The mixture was refluxed under heating for 1 hour. After cooling, the reaction mixture was washed with water, dried over anhydrous magnesium sulfate and concentrated under reduced pressure. The obtained oil was purified by silica gel column chromatography using a mixed solvent of n-hexane:ethyl acetate=2:1 as a developing solvent to give the object compound as an oil, melting point 85°–89° C.

$[α]_D$=−31.6° (c=1%, methanol)

Preparative Example 11

(R)-N,N-Dibenzyl-3-hydroxymethyl-1-((S)-α-methylbenzyl)-5-oxopyrrolidine-3-carboxamide was treated in the same manner as in Preparative Example 10 to give (S)-N,N-dibenzyl-3-fluoromethyl-1-((S)-α-methylbenzyl)-5-oxopyrrolidine-3-carboxamide, melting point 113°–115° C.

$[α]_D$=−88.6° (c=1%, methanol)

Preparative Example 12

(S)-3-(N,N-Dibenzylaminomethyl)-3-fluoromethyl-1-((S)-α-methylbenzyl)pyrrolidine Lithium aluminum hydride (1.23 g) was suspended in tetrahydrofuran (20 ml), and a solution of (R)-N,N-dibenzyl-3-fluoromethyl-1-((S)-α-methylbenzyl)-5-oxopyrrolidine-3-carboxamide (7.2 g) in tetrahydrofuran (20 ml) was dropwise added under water-cooling. The mixture was stirred at room temperature for 1 hour and refluxed under stirring for 3 hours. After cooling, a mixed solvent of water (1.23 ml) and tetrahydrofuran (5 ml) and 5 ml of an aqueous solution of sodium hydroxide (0.18 g) were dropwise added, and the mixture was allowed to stand overnight. The solution was filtered through Celite, and the filtrate was concentrated under reduced pressure and purified by silica gel column chromatography using a mixed solvent of n-hexane:ethyl acetate=2:1 as a developing solvent to give the object compound as an oil.

$[α]_D$=−13.2° (c=1%, methanol)

Preparative Example 13

(R)-3-(N,N-Dibenzylaminomethyl)-3-fluoromethyl-1-((S)-α-methylbenzyl)pyrrolidine An oily object compound was obtained from (R)-N,N-dibenzyl-3-fluoromethyl-1-((S)-α-methylbenzyl)-5-oxopyrrolidine-3-carboxamide in the same manner as in Preparative Example 12.

$[α]_D$=−44.8° (c=1%, methanol)

Preparative Example 14

(S)-3-Aminomethyl-3-fluoromethylpyrrolidine (S)-3-(N,N-Dibenzylaminomethyl)-3-fluoromethyl-1-((S)-α-methylbenzyl)pyrrolidine (3.84 g) was dissolved in ethanol (40 ml) and 10% palladium-carbon (1.54 g) and hydrazine monohydrate (2.08 g) were added. The mixture was refluxed for 2 hours. The reaction mixture was filtered through Celite and the filtrate was concentrated under reduced pressure to give the object compound as an oil.

$[α]_D$=+7.8° (c=1%, methanol)

Preparative Example 15

(R)-3-Aminomethyl-3-fluoromethylpyrrolidine

An oily object compound was obtained from (R)-3-(N,N-dibenzylaminomethyl)-3-fluoromethyl-1-((S)-α-methylbenzyl)pyrrolidine in the same manner as in Preparative Example 14.

$[α]_D$=−7.9° (c=1%, methanol)

Preparative Example 16

(R)-3-Ethoxycarbonyl-1((S)-α-methylbenzyl)-5-oxopyrrolidine-3-carboxylic acid

Acetone (340 ml) and a 0.05M potassium phosphate buffer (pH 8.0, 3100 ml) were added to diethyl 1-((S)-α-methylbenzyl)-5-oxopyrrolidine-3,3-dicarboxylate (23 g) obtained in Preparative Example 6, and an esterase (6.5 ml, Sigma) was added. The mixture was stirred at 30° C. for 7 hours. The reaction mixture was made acidic with dilute hydrochloric acid and the resulting mixture was extracted three times with chloroform (200 ml). The extract was concentrated under reduced pressure to give the object compound, melting point 137°–139° C. (decomposition).

$[α]_D$=−39° (c=1%, methanol)

Preparative Example 17

Ethyl (R)-3-(N,N-dibenzylcarbamoyl)-1-((S)-α-methylbenzyl)-5-oxopyrrolidine-3-carboxylate The object compound was obtained in the same manner as in Preparative Example 8 from (R)-3-ethoxycarbonyl-1-((S)-α-methylbenzyl)-5-oxopyrrolidine-3-carboxylic acid obtained in Preparative Example 16.

$[α]_D$=−10.9° (c=1%, methanol)

Preparative Example 18

(S)-N,N-Dibenzyl-3-hydroxymethyl-1-((S)-α-methylbenzyl)-5-oxopyrrolidine-3-carboxamide The object compound was obtained in the same manner as in Preparative Example 9 from ethyl (R)-3-(N,N-dibenzylcarbamoyl)-1-((S)-α-methylbenzyl)-5-oxopyrrolidine-3-carboxylate obtained in Preparative Example 17, melting point 135°–137° C.

$[α]_D$=−35.9° (c=1%, methanol)

Preparative Example 19

Diethyl 1-((R)-α-methylbenzyl)-5-oxopyrrolidine-3,3-dicarboxylate

The object compound was obtained in the same manner as in Preparative Example 6 from D-(+)-α-methylbenzylamine.

$[α]_D$=+27.6° (c=1%, methanol)

Preparative Example 20

(R)-3-Ethoxycarbonyl-1-((R)-α-methylbenzyl)-5-oxopyrrolidine-3-carboxylic acid

The object compound was obtained in the same manner as in Preparative Example 16 from diethyl 1-((R)-α-methylbenzyl)-5-oxopyrrolidine-3,3-dicarboxylate obtained in Preparative Example 19, melting point 163° C. (decomposition).

$[α]_D$=+39.7° (c=1%, methanol)

Preparative Example 21

(RS)-3-Ethoxycarbonyl-1-((R)-α-methylbenzyl)-5-oxopyrrolidine-3-carboxylic acid

The object compound was obtained in the same manner as in Preparative Example 7 from diethyl 1-(R)-α-methylbenzyl)-5-oxopyrrolidine-3,3-dicarboxylate obtained in Preparative Example 19.

Preparative Example 22

Ethyl (RS)-3-(N-benzyl-N-methylcarbamoyl)-1-((R)-α-methylbenzyl)-5-oxopyrrolidine-3-carboxylate (RS)-3-Ethoxycarbonyl-1-((R)-α-methylbenzyl)-5-oxopyrrolidine-3-carboxylic acid (32.1 g) obtained in Preparative Example 21 was dissolved in chloroform (100 ml), and thionyl chloride (15 ml) and one drop of N,N-dimethylforimamide were added. The mixture was refluxed for 2 hours and the reaction mixture was concentrated under reduced pressure. The obtained oil was dissolved in toluene (39 ml), and the mixture was dropwise added to a solution of N-methylbenzylamine (15.3 g) and triethylamine (12.7 g) in toluene (130 ml) under ice-cooling. The mixture was refluxed for 2 hours. The reaction mixture was washed with water, sodium hydrogencarbonate, 10% aqueous hydrochloric acid and water, and dried over anhydrous magnesium sulfate to give the object compound.

NMR(CDCl$_3$, 100 MHz) δ: 7.40–6.72(m, 10H), 5.46(q, 1H), 4.88–4.19 (m,2H), 4.04(q,2H), 3.34–2.82(m,4H), 2.68 (s,3H), 1.58 and 1.57(d,3H), 1.20 and 1.06(t,3H).

Preparative Example 23

(R)-N-Benzyl-3-hydroxymethyl-N-methyl-1-((R)-α-methylbenzyl)-5-oxopyrrolidine-3-carboxamide and (S)-N-benzyl-3-hydroxymethyl-N-methyl-1-((R)-α-methylbenzyl)-5-oxopyrrolidine-3-carboxamide Ethyl (RS)-3-(N-benzyl-N-methylcarbamoyl)-1-((R)-α-methylbenzyl)-5-oxopyrrolidine-3-carboxylate (39 g) obtained in Preparative Example 22 was dissolved in methanol (590 ml) and sodium borohydride (40 g) was portionwise added under water-cooling. The mixture was allowed to stand overnight at room temperature and the reaction mixture was concentrated under reduced pressure. Ethyl acetate (170 ml) was added to the concentrate, and the mixture was washed with water and dried over anhydrous magnesium sulfate. The solvent was distilled away to give a mixture of diastereomers. The mixture was separated and purified by silica gel column chromatography (developing solvent, chloroform:ethyl acetate=1:1) to give (R)-N-benzyl-3-hydroxymethyl-N-methyl-1-((R)-α-methylbenzyl)-5-oxopyrrolidine-3-carboxamide ([α]$_D$=+29.0° (c=1%, methanol)) and (S)-N-benzyl-3-hydroxymethyl-N-methyl-1-((R)-α-methylbenzyl)-5-oxopyrrolidine-3-carboxamide ([α]$_D$=+79.2° (c=1%, methanol)).

Preparative Example 24

(S)-N-Benzyl-3-fluoromethyl-N-methyl-1-((R)-α-methylbenzyl)-5-oxopyrrolidine-3-carboxamide (R)-N-Benzyl-3-hydroxymethyl-N-methyl-1-((R)-α-methylbenzyl)-5-oxopyrrolidine-3-carboxamide (11.5 g) was dissolved in chloroform (120 ml) and hexafluoropropenediethylamine (14.2 g) was added. The mixture was refluxed for 1.5 hours. After cooling, the reaction mixture was washed with water and sodium hydrogencarbonate, dried over anhydrous magnesium sulfate and concentrated under reduced pressure. The obtained oil was purified by silica gel column chromatography (developing solvent, chloroform:ethyl acetate=1:1) to give the object compound as crystals, melting point 98°–104° C.

[α]$_D$=+27.6° (c=1%, methanol)

Preparative Example 25

(R)-3-(N-Benzyl-N-methylaminomethyl)-3-fluoromethyl-1-((R)-α-methylbenzyl)pyrrolidine A solution of (S)-N-benzyl-3-fluoromethyl-N-methyl-1-((R)-α-methylbenzyl)-5-oxopyrrolidine-3-carboxamide (5.37 g) in tetrahydrofuran (60 ml) was dropwise added to a solution of lithium aluminum hydride (1.1 g) in tetrahydrofuran (60 ml) at room temperature, and the mixture was stirred. The mixture was refluxed for 3 hours and cooled with ice. A mixture of tetrahydrofuran (12 ml) and water (1.2 ml) was dropwise added, and a mixture of 15% aqueous solution of sodium hydroxide (1.2 ml) and water (3.6 ml) was added, followed by stirring. The reaction mixture was filtered through Celite, and the filtrate was concentrated under reduced pressure and extracted with ethyl acetate. The extract was washed with a saturated aqueous solution of sodium chloride, dried over anhydrous magnesium sulfate, and concentrated under reduced pressure. The obtained oil was purified by silica gel column chromatography (developing solvent, n-hexane:ethyl acetate: 9:1) to give the object compound as a yellow oil.

[α]$_D$=+33.5° (c=1%, methanol)

Preparative Example 26

(R)-3-Fluoromethyl-3-methylaminomethylpyrrolidine (R)-3-(N-Benzyl-N-methylaminomethyl)-3-fluoromethyl-1-((R)-α-methylbenzyl)pyrrolidine (2.05 g) was dissolved in ethanol (55 ml), and 10% palladium-carbon (0.8 g) and hydrazine monohydrate (0.90 g) were added at room temperature. The mixture was refluxed for 40 minutes. The reaction mixture was filtered through Celite, and the filtrate was concentrated under reduced pressure to give the object compound as a yellow oil.

[α]$_D$=−8.13° (c=1%, methanol)

Preparative Example 27

Ethyl (R)-3-benzylcarbamoyl-1-((S)-α-methylbenzyl)-5-oxopyrrolidine-3-carboxylate (R)-3-Ethoxycarbonyl-1-((S)-α-methylbenzyl)-5-oxopyrrolidine-3-carboxylic acid (10 g) was dissolved in tetrahydrofuran (100 ml). Hydroxybenztriazole (0.89 g) was added and the mixture was stirred. Dicyclohexylcarbodiimide (6.76 g) and benzylamine (3.86 g) were added under ice-cooling, and the mixture was stirred at room temperature for 30 minutes. The reaction mixture was allowed to stand for 2 days and filtered through Celite. The filtrate was concentrated under reduced pressure. Ethyl acetate was added, and the mixture was washed with an aqueous solution of potassium carbonate, water, dilute hydrochloric acid and a saturated aqueous solution of sodium chloride, and dried over anhydrous magnesium sulfate. The obtained oil was purified by silica gel column chromatography (developing solvent, n-hexane:ethyl acetate=4:1) to give the object compound as a pale yellow oil.

NMR(CDCl$_3$,100 MHz) δ: 8.50–8.30(bs,1H), 7.30–7.10 (m,10H), 5.30(q,1H), 4.40–4.30(m,2H), 4.10–3.90(m, 3H), 3.70(ABq,1H), 3.00(ABq,2H), 1.50(d,3H), 1.05(t,3H)

Preparative Example 28

(S)-N-Benzyl-3-hydroxymethyl-1-((S)-α-methylbenzyl)-5-oxopyrrolidine-3-carboxamide Ethyl (R)-3-benzylcarbamoyl-1-((S)-α-methylbenzyl)-5-oxopyrrolidine-3-carboxylate (12 g) was dissolved in methanol (120 ml) and sodium borohydride (10 g) was added under ice-cooling. The mixture was stirred for 2 hours under water-cooling. The mixture was allowed to stand at room temperature overnight and concentrated under reduced pressure. The residue was extracted with chloroform and dried over anhydrous magnesium sulfate. The obtained oil was purified by silica gel chromatography (developing solvent:chloroform). After crystallization, the resulting product was washed with isopropyl ether to give the object compound as colorless crystals, melting point 122°–124° C.

$[α]_D = -35.0°$ (c=1%, methanol)

Preparative Example 29

(R)-N-Benzyl-3-fluoromethyl-1-((S)-α-methylbenzyl)-5-oxopyrrolidine-3-carboxamide (S)-N-Benzyl-3-hydroxymethyl-1-((S)-α-methylbenzyl)-5-oxopyrrolidine-3-carboxamide (11.46 g) was dissolved in chloroform (60 ml) and hexafluoropropenediethylamine (14.8 g) was added. The mixture was refluxed for 50 minutes. Ice water (100 ml) was added under water-cooling and the mixture was extracted twice with chloroform. The extract was dried over anhydrous sodium sulfate and concentrated under reduced pressure. The obtained oil was purified by silica gel chromatography (developing solvent:chloroform) to give the object compound as crystals, melting point 114°–116° C.

Preparative Example 30

(R)-N-Benzyl-3-fluoromethyl-N-methyl-1-((S)-α-methylbenzyl)-5-oxopyrrolidine-3-carboxamide A solution of (R)-N-benzyl-3-fluoromethyl-1-((S)-α-methylbenzyl)-5-oxopyrrolidine-3-carboxamide (3.72 g) in dimethylformamide (30 ml) was added to a solution of 60% sodium hydride (0.51 g) in dimethylformamide (20 ml) under ice-cooling, and the mixture was stirred at room temperature for 1 hour. Methyl iodide (0.7 ml) was added under ice-cooling, and the mixture was stirred at room temperature for 5.5 hours. Ice water (200 ml) was added to the reaction mixture, and the mixture was extracted twice with ethyl acetate, washed with saturated brine, and dried over anhydrous magnesium sulfate. The obtained oil was purified by silica gel column chromatography (developing solvent:chloroform) to give the object compound as crystals, melting point 95°–98° C.

$[α]_D = -28.8°$ (c=1%, methanol)

Preparative Example 31

(S)-3-(N-Benzyl-N-methylaminomethyl)-3-fluoromethyl-1-((S)-α-methylbenzyl)pyrrolidine The object compound was obtained as an oil, in the same manner as in Preparative Example 25 from (R)-N-benzyl-3-fluoromethyl-N-methyl-1-((S)-α-methylbenzyl)-5-oxopyrrolidine-3-carboxamide.

$[α]_D = -35.6°$ (c=1%, methanol)

Preparative Example 32

(S)-3-Fluoromethyl-3-methylaminomethylpyrrolidine

The object compound was obtained as a yellow oil, in the same manner as in Preparative Example 26 from (S)-3-(N-benzyl-N-methylaminomethyl)-3-fluoromethyl-1-((S)-α-methylbenzyl)pyrrolidine.

$[α]_D = +7.47°$ (c=1%, methanol)

Preparative Example 33

(S)-3-(N,N-Dibenzylaminomethyl)-3-fluoromethyl-1-((S)-α-methylbenzyl)pyrrolidine (R)-N,N-Dibenzyl-3-fluoromethyl-1-((S)-α-methylbenzyl)-5-oxopyrrolidine-3-carboxamide (14 g) obtained in Preparative Example 10 was dissolved in tetrahydrofuran (40 ml) and the solution was added to a 1N borane-tetrahydrofuran solution (126 ml). The mixture was refluxed for 4 hours. A 3N hydrochloric acid solution (48 ml) was dropwise added to the reaction mixture under ice-cooling, and the mixture was refluxed for 2 hours with stirring. The reaction mixture was made alkaline with an aqueous solution of sodium hydroxide, and extracted with ethyl acetate. The extract was washed with water, dried, concentrated and purified by silica gel column chromatography to give the object compound as an oil.

Preparative Example 34

(S)-N,N-Dibenzyl-3-fluoromethyl-1-((S)-α-methylbenzyl)-5-oxopyrrolidine-3-carboxamide obtained in Preparative Example 11 was treated in the same manner as in Preparative Example 33 to give (R)-3-(N,N-dibenzylaminomethyl)-3-fluoromethyl-1-((S)-α-methylbenzyl)pyrrolidine.

Preparative Example 35

(S)-3-(N,N-dibenzylaminomethyl)-3-fluoromethyl-1-((S)-α-methylbenzyl)pyrrolidine Sodium borohydride (12.2 g) was added to a solution of (R)-N,N-dibenzyl-3-fluoromethyl-1-((S)-α-methylbenzyl)-5-oxopyrrolidine-3-carboxamide (28.6 g) obtained in Preparative Example 10 in tetrahydrofuran (300 ml), and a solution of conc. sulfuric acid (8.6 ml) in tetrahydrofuran (100 ml) was dropwise added at not more than 5° C. over 1 hour. 3N Hydrochloric acid (78 ml) was dropwise added under ice-cooling and the mixture was refluxed for 1 hour with stirring. The reaction mixture was made alkaline by an aqueous solution of sodium hydroxide, and extracted with ethyl acetate, washed with water, dried, concentrated, and purified by silica gel column chromatography to give the object compound as an oil.

Preparative Example 36

(S)-N,N-Dibenzyl-3-fluoromethyl-1-((S)-α-methylbenzyl)-5-oxopyrrolidine-3-carboxamide obtained in Preparative Example 11 was treated in the same manner as in Preparative Example 35 to give (R)-3-(N,N-dibenzylaminomethyl)-3-fluoromethyl-1-((S)-α-methylbenzyl)pyrrolidine.

Preparative Example 37

(1) (S)-3-(N,N-Dibenzylaminomethyl)-1-ethoxycarbonyl-3-fluoromethylpyrrolidine (S)-3-(N,N-Dibenzylaminomethyl)-3-fluoromethyl-1-((S)-α-methylbenzyl)pyrrolidine (62 g) obtained in Preparative Example 12 was dissolved in toluene (620 ml), and ethyl chloroformate (40 ml) was added. The mixture was stirred at 75°–80° C. for 5 hours. The insoluble matter was removed, and the reaction mixture was sequentially washed with an aqueous solution of potassium carbonate, water, a 1N aqueous solution of citric acid and water, dried, and concentrated to give the object compound as an oil.

NMR(CDCl$_3$) δ: 1.22(t, 3H), 1.5–1.7(m, 2H), 2.62(s, 2H), 2.8–3.4(m,4H), 3.59(ABq,4H), 4.07(q, 2H), 4.30(d,2H), 7.15–7.35(m,10H).

(2) (R)-3-(N,N-Dibenzylaminomethyl)-3-fluoromethylpyrrolidine (S)-3-(N,N-Dibenzylaminomethyl)-1-ethoxycarbonyl-3-fluoromethylpyrrolidine (52 g) was dissolved in isopropyl alcohol (500 ml), and sodium hydroxide (27 g) was added. The mixture was refluxed for 40 hours with stirring. After concentration, water (300 ml) was added to the concentrate and the mixture was extracted with ethyl acetate. The organic layer was washed with water, dried and concentrated to give the object compound as an oil.

NMR(CDCl$_3$) δ: 1.40–1.60(m,2H), 2.23(bs,1H), 2.50–2.90(m,5H), 3.60(s,4H), 4.34(d,2H), 7.15–7.35(m, 10H).

Preparative Example 38

(1) (R)-3-(N,N-Dibenzylaminomethyl)-3-fluoromethyl-1-((S)-α-methylbenzyl)pyrrolidine obtained in Preparative Example 13 was treated in the same manner as in Preparative Example 37 (1) to give (R)-3-(N,N-dibenzylaminomethyl)-1-ethoxycarbonyl-3-fluoromethylpyrrolidine.

NMR(CDCl$_3$) δ: 1.21(t,3H), 1.55–1.75(m,2H), 2,61(s, 2H), 2.80–3.40(m,4H), 3.58(ABq,4H), 4.06(q,2H), 4.30(d, 2H), 7.15–7.35(m,10H)

(2) (R)-3-(N,N-Dibenzylaminomethyl)-1-ethoxycarbonyl-3-fluoromethylpyrrolidine was treated in the same manner as in Preparative Example 37 (2) to give (S)-3-(N,N-dibenzylaminomethyl)-3-fluoromethylpyrrolidine.

NMR(CDCl$_3$) δ: 1.40–1.60(m,2H), 2.35(s,1H)), 2.55–2.9 (m,5H)), 3.60(s,4H), 4.33(d,2H), 7.15–7.35(m, 10H).

Preparative Example 39

(1) (R)-3-(N,N-Dibenzylcarbamoyl)-1-((S)-α-methylbenzyl)-5-oxopyrrolidine-3-carboxylic acid Ethyl (R)-3-(N,N-dibenzylcarbamoyl)-1-((S)-α-methylbenzyl)-5-oxopyrrolidine-3-carboxylate (48.5 g) obtained in Preparative Example 17 was dissolved in methanol (250 ml), and a solution of sodium hydroxide (16 g) in water (125 ml) was added. The mixture was stirred at 40° C. for 2 hours. After concentration, the reaction mixture was washed with toluene, made acidic with 6N hydrochloric acid and extracted with chloroform. The extract was washed with water, dried, concentrated, and crystallized from isopropyl ether. The crystals were collected by filtration to give the object compound, melting point 138°–139° C.

(2) (S)-3-N,N-Dibenzyl-3-hydroxymethyl-1-((S)-α-methylbenzyl)-5-oxopyrrolidine-3-carboxamide N,N-Dimethylformamide (877 mg) was dissolved in dichloromethane (20 ml), and oxalyl chloride (2.93 ml) was dropwise added under ice-cooling. The mixture was stirred at room temperature for 2 hours. After concentration, acetonitrile (10 ml) and tetrahydrofuran (20 ml) were added, and a solution of (R)-3-(N,N-dibenzylcarbamoyl)-1-((S)-α-methylbenzyl)-5-oxopyrrolidine-3-carboxylic acid (4.57 g) in tetrahydrofuran (10 ml) was dropwise added under ice-cooling. The mixture was stirred at said temperature for 1 hour. A solution of sodium borohydride (908 mg) in N,N-dimethylformamide (25 ml) was dropwise added under ice-cooling, and the mixture was stirred at said temperature for 1.5 hours. A 2N hydrochloric acid (20 ml) was added, and the mixture was extracted with ethyl acetate. The extract was washed with water, dried, concentrated and crystallized from isopropyl ether. The crystals were collected by filtration to give the object compound.

Preparative Example 40

1-Benzyl-3-(N,N-dibenzylcarbamoyl)-5-oxopyrrolidine-3-carboxylic acid obtained in Preparative Example 5 (1) was treated in the same manner as in Preparative Example 39 (2) to give 1-benzyl-N,N-dibenzyl-3-hydroxymethyl-5-oxopyrrolidine-3-carboxamide, melting point 127°–129° C.

Example 1

7-(3-Aminomethyl-3-fluoromethylpyrrolidin-1-yl)-1-cyclopropyl-6-fluoro-1,4-dihydro-8-methoxy-4-oxo-3-quinolinecarboxylic acid 3-Aminomethyl-3-fluoromethylpyrrolidine (0.660 g) obtained in Preparative Example 2 (5) and 1-cyclopropyl-6,7-difluoro-1,4-dihydro-8-methoxy-4-oxo-3-quinolinecarboxylic acid-BF$_2$ chelate (0.69 g) were dissolved in acetonitrile (5 ml), and the mixture was stirred at room temperature overnight. The solvent was distilled away under reduced pressure and ethanol was added to allow crystallization. Methanol (80 ml) and triethylamine (5 ml) were added to the obtained crystals. The mixture was refluxed for 2 hours. The solvent was distilled away under reduced pressure and ethanol was added to allow crystallization. The crystals were recrystallized from ethanol to give 0.38 g of the object compound, melting point 192°–194° C.

Example 2

Methyl 7-(3-aminomethyl-3-fluoromethylpyrrolidin-1-yl)-1-cyclopropyl-6-fluoro-1,4-dihydro-8-methoxy-4-oxo-3-quinolinecarboxylate 7-(3-Aminomethyl-3-fluoromethylpyrrolidin-1-yl)-1-cyclopropyl- 6-fluoro-1,4-dihydro-8-methoxy-4-oxo-3-quinolinecarboxylic acid (8.9 g) obtained in Example 1 was suspended in methanol (100 ml) and thionyl chloride (3.2 ml) was dropwise added with stirring under ice-cooling. After the dropwise addition, the mixture was refluxed overnight. Methanol and excess thionyl chloride were distilled away under reduced pressure. The residue was dissolved in water and the solution was made alkaline with potassium carbonate. The mixture was extracted twice with chloroform, dried and concentrated to dryness to give 9.8 g of the object compound, melting point 143°–145° C.

Example 3

(1) Methyl (S)-(+)-7-(3-aminomethyl-3-fluoromethylpyrrolidin-1-yl)-1-cyclopropyl-6-fluoro-1,4-dihydro-8-methoxy-4-oxo-3-quinolinecarboxylate A solution of (R)-O-methylmandelic acid (2.2 g) in methanol (8 ml) was added to a solution of the compound (8.1 g) obtained in Example 2 in methanol (32 ml), and the mixture was left standing at room temperature for 3 days. The precipitated crystals were collected by filtration and recrystallized 4 times from methanol. The obtained crystals were suspended in water, and the suspension was made alkaline with potassium carbonate and extracted with chloroform. The extract was washed with water, dried and concentrated to give 1.1 g of the object compound, melting point 150°–152° C., optical purity not less than 95% ee (HPLC).

(2) (S)-(+)-7-(3-Aminomethyl-3-fluoromethylpyrrolidin-1-yl)-1-cyclopropyl-6-fluoro-1,4-dihydro-8-methoxy-4-oxo-3-quinolinecarboxylic acid An optically active ester (1.1 g) obtained in (1) was dissolved in methanol (10 ml), and an aqueous solution (2 ml) of potassium hydroxide (0.22 g) was added. The mixture was stirred at room temperature overnight. The solvent was distilled away under reduced pressure. The residue was dissolved in water and its pH was adjusted to 7 with acetic acid. The mixture was extracted with chloroform, dried and concentrated. The residue was recrystallized from ethanol to give 0.42 g of the object compound as white crystals, melting point 186°–188° C.

$[\alpha]_D$=–40.1° (1.50% methanol-chloroform), optical purity not less than 95% ee (HPLC).

Example 4

(1) Methyl (R)-(–)-7-(3-aminomethyl-3-fluoromethylpyrrolidin-1-yl)-1-cyclopropyl-6-fluoro-1,4-dihydro-8-methoxy-4-oxo-3-quinolinecarboxylate The ester recovered from the mother liquor obtained in Example 3 (1) was dissolved in methanol (28 ml), and a solution of (S)-O-methylmandelic acid (1.9 g) in methanol (7 ml) was added. The mixture was left standing at room temperature overnight. The precipitated crystals were collected by filtration and recrystallized 3 times from methanol. The obtained crystals were suspended in water, and the suspension was made alkaline with potassium carbonate. The mixture was extracted with chloroform. The extract was washed with water, dried and concentrated to give 1.1 g of the object compound, melting point 151°–152° C., optical purity not less than 95% ee (HPLC).

(2) (R)-(–)-7-(3-Aminomethyl-3-fluoromethylpyrrolidin-1-yl)-1-cyclopropyl-6-fluoro-1,4-dihydro-8-methoxy-4-oxo-3-quinolinecarboxylic acid The optically active ester (1.1 g) obtained in (1) was reacted in the same manner as in Example 3 (2) to give 0.55 g of the object compound as white crystals, melting point 187°–189° C.

$[\alpha]_D$=–39.4° (1.50% methanol-chloroform), optical purity not less than 95% ee (HPLC).

Example 5

(S)-(+)-7-(3-Aminomethyl-3-fluoromethylpyrrolidin-1-yl)-1-cyclopropyl-6-fluoro-1,4-dihydro-8-methoxy-4-oxo-3-quinolinecarboxylic acid (S)-3-Aminomethyl-3-fluoromethylpyrrolidine (0.88 g) obtained in Preparative Example 14, triethylamine (0.45 g) and 1-cyclopropyl-6,7-difluoro-1,4-dihydro-8-methoxy-4-oxo-3-quinolinecarboxylic acid-$BF_2$ chelate (1.52 g) were treated in the same manner as in Example 1 and recrystallized from chloroform-ethanol to give the object compound, melting point 188°–190° C.

$[\alpha]_D$=+24.9° (c=1%, acetic acid).

Example 6

(R)-(–)-7-(3-Aminomethyl-3-fluoromethylpyrrolidin-1-yl)-1-cyclopropyl-6-fluoro-1,4-dihydro-8-methoxy-4-oxo-3-quinolinecarboxylic acid (R)-3-Aminomethyl-3-fluoromethylpyrrolidine (0.88 g) obtained in Preparative Example 15, triethylamine (0.45 g) and 1-cyclopropyl- 6,7-difluoro-1,4-dihydro-8-methoxy-4-oxo-3-quinolinecarboxylic acid-$BF_2$ chelate (1.52 g) were treated in the same manner as in Example 1 and recrystallized from chloroform-ethanol to give the object compound, melting point 189°–191° C.

$[\alpha]_D$=–25.3° (c=1%, acetic acid).

Example 7

1-Cyclopropyl-6-fluoro-7-(3-fluoromethyl-3-methylaminomethylpyrrolidin-1-yl)-1,4-dihydro-8-methoxy-4-oxo-3-quinolinecarboxylic acid 3-Fluoromethyl-3-methylaminomethylpyrrolidine (1.46 g) obtained in Preparative Example 4 (2) and 1-cyclopropyl- 6,7-difluoro-1,4-dihydro-8-methoxy-4-oxo-3-quinolinecarboxylic acid-$BF_2$ chelate (1.37 g) were treated in the same manner as in Example 1 and recrystallized from ethanol-ammonia to give 0.51 g of the object compound, melting point 208°–210° C.

Example 8

(R)-(–)-1-Cyclopropyl-6-fluoro-7-(3-fluoromethyl-3-methylaminomethylpyrrolidin-1-yl)-1,4-dihydro-8-methoxy-4-oxo-3-quinolinecarboxylic acid (R)-3-Fluoromethyl-3-methylaminomethylpyrrolidine (0.97 g) obtained in Preparative Example 26 was dissolved in acetonitrile (26 ml), and triethylamine (0.62 ml) and 1-cyclopropyl-6,7-difluoro-1,4-dihydro-8-methoxy-4-oxo-3-quinolinecarboxylic acid-$BF_2$ chelate (1.52 g) were added. The mixture was treated in the same manner as in Example 1 and recrystallized from ethanol-aqueous ammonia to give the object compound as colorless crystals, melting point 156°–157° C.

$[\alpha]_D$=–51.9° (c=1%, acetic acid)

Example 9

(S)-(+)-1-Cyclopropyl-6-fluoro-7-(3-fluoromethyl-3-methylaminomethylpyrrolidin-1-yl)-1,4-dihydro-8-methoxy-4-oxo-3-quinolinecarboxylic acid (S)-3-Fluoromethyl-3-methylaminomethylpyrrolidine obtained in Preparative Example 32 was treated in the same manner as in Example 7 to give the object compound as colorless crystals, melting point 150°–152° C.

$[\alpha]_D$=+59.3° (c=1%, chloroform:methanol=1:1)

Example 10

(1) (S)-1-Cyclopropyl-7-(3-(N,N-dibenzylaminomethyl)-3-fluoromethylpyrrolidin-1-yl)-6-fluoro-1,4-dihydro-8-methoxy-4-oxo-3-quinolinecarboxylic acid A mixture of (R)-3-(N,N-dibenzylaminomethyl)-3-fluoromethylpyrrolidine (23 g) obtained in Preparative Example 37 (2), 1-cyclopropyl-6,7-difluoro-1,4-dihydro-8-methoxy-4-oxo-3-quinolinecarboxylic acid-$BF_2$ chelate (21 g), triethylamine (6.5 g) and acetonitrile (200 ml) was stirred for 14 hours. After concentration, ethanol was added and the obtained crystals were collected by filtration. Methanol (200 ml), chloroform (100 ml) and triethylamine (50 ml) were added to the crystals and the mixture was refluxed for 4 hours. After concentration, ethanol was added and the obtained crystals were collected by filtration to give the object compound.

(2) (S)-7-(3-Aminomethyl-3-fluoromethylpyrrolidin-1-yl)-1-cyclopropyl-6-fluoro-1,4-dihydro-8-methoxy-4-oxo-3-quinolinecarboxylic acid (S)-1-Cyclopropyl-7-(3-(N,N-dibenzylaminomethyl)-3-fluoromethylpyrrolidin-1-yl)-6-fluoro-1,4-dihydro-8-methoxy-4-oxo-3-quinolinecarboxylic acid (19.58 g) was dissolved in ethanol (300 ml), and 10% palladium-carbon (3.9 g) and hydrazine hydrate (5.0 g) were added. The mixture was refluxed with stirring for 4 hours. The precipitated crystals were dissolved in a 2N aqueous solution of sodium hydroxide. The mixture was filtrated to remove the catalyst. After concentration, water (100 ml) was added and the pH of the solution was adjusted to 7 with dilute hydrochloric acid. The precipitated crystals were collected by filtration to give the object compound, melting point 188°–190° C.

Example 11

(S)-7-(3-Aminomethyl-3-fluoromethylpyrrolidin-1-yl)-1-cyclopropyl-6-fluoro-1,4-dihydro-8-methoxy-4-oxo-3-quinolinecarboxylic acid (S)-1-Cyclopropyl-7-(3-(N,N-dibenzylaminomethyl)-3-fluoromethylpyrrolidin-1-yl)-6-fluoro-1,4-dihydro-8-methoxy-4-oxo-3-quinolinecarboxylic acid (7.51 g) obtained in Example 10 (1) was suspended in ethanol (40 ml) and methanol (40 ml). 6N Hydrochloric acid (4.3 ml) and 10% palladium-carbon (1.5 g) were added and hydrogen was bloom thereto at 40° C. After the completion of the reaction, the catalyst was removed by filtration and the filtrate was concentrated. Acetone (170 ml) was added and the precipitated hydrochloride of the object compound was collected by filtration as crystals, melting point 213°–217° C.

The obtained hydrochloride was dissolved in water (100 ml) and the pH of the solution was adjusted to 7 with a 4N aqueous solution of sodium hydroxide. The precipitated crystals were collected by filtration to give the object compound, melting point 196°–198° C.

Example 12

(1) (S)-1-Cyclopropyl-7-(3-(N,N-dibenzylaminomethyl)-3-fluoromethylpyrrolidin-1-yl)-6,8-difluoro-1,4-dihydro-4-oxo-3-quinolinecarboxylic acid 1-Cyclopropyl-6,7,8-trifluoro-1,4-dihydro-4-oxo-3-quinolinecarboxylic acid (5 g), (R)-3-N,N-dibenzylaminomethyl-3-fluoromethylpyrrolidine (6.6 g) and triethylamine (2.0 g) were dissolved in acetonitrile (75 ml), and the mixture was stirred for 7.5 hours. After cooling, the precipitated crystals were collected by filtration to give the object compound as pale-yellow crystals, melting point 185°–186° C.

$[\alpha]_D$=+4.3° (c=1%, chloroform)

(2) (S)-1-Cyclopropyl-7-(3-(N,N-dibenzylaminomethyl)-3-fluoromethylpyrrolidin-1-yl)-6-fluoro-1,4-dihydro-8-methoxy-4-oxo-3-quinolinecarboxylic acid Dimethylacetamide was added to (S)-1-cyclopropyl-7-(3-(N,N-dibenzylaminomethyl)-3-fluoromethylpyrrolidin-1-yl)-6,8-difluoro-1,4-dihydro-4-oxo-3-quinolinecarboxylic acid (3 g) and sodium methoxide (1.4 g), and the mixture was stirred at 100° C. for 2 hours. After cooling, water was added and the pH of the solution was adjusted to 6.0 with acetic acid. The mixture was extracted with ethyl acetate. The extract was washed with water, dried, concentrated and crystallized from isopropyl ether-ethanol. The crystals were collected by filtration. The crystals were recrystallized from ethanol to give the object compound, melting point 132°–133° C.

$[\alpha]_D$=+42.0° (c=1%, chloroform)

Example 13

(1) Ethyl (S)-4-(3-(N,N-dibenzylaminomethyl)-3-fluoromethylpyrrolidin-1-yl)-2,3,5-trifluorobenzoylacetate Ethyl 2,3,4,5-tetrafluorobenzoylacetate (13.2 g), (R)-3-(N,N-dibenzylaminomethyl)-3-fluoromethylpyrrolidine (18.2 g) and triethylamine (5.6 g) were dissolved in dimethyl sulfoxide (54 ml), and the mixture was stirred at 100° C. for 5 hours. After cooling, water was added and the mixture was extracted with ethyl acetate. The extract was washed with water, dried and concentrated. The obtained oil was purified by silica gel column chromatography (developing solvent; chloroform:methanol=50:1) to give the object compound as a yellow oil.

$[\alpha]_D$=−10.5° (c=1%, chloroform)

NMR(CDCl$_3$) δ: 1.36(t,3H), 1.70(t,3H), 2.65(s,2H), 3.55 (m,4H), 3.60(s,4H)), 3.86(d,2H), 4.00–4.38(m,3H), 4.63(s, 1H), 7.25(m,11H)

(2) Ethyl (S)-2-(4-(3-(N,N-dibenzylaminomethyl)-3-fluoromethylpyrrolidin-1-yl)-2,3,5-trifluorobenzoyl)-3-cyclopropylaminoacrylate Ethyl (S)-4-(3-(N,N-dibenzylaminomethyl)-3-fluoromethylpyrrolidin-1-yl)-2,3,5-trifluorobenzoylacetate (5.2 g) and dimethylformamide dimethyl acetal (2.5 ml) were dissolved in dry toluene (30 ml), and the mixture was refluxed for 8 hours. After concentration, the residue was dissolved in dry ethanol (15 ml), and cyclopropylamine (0.53 g) was added. The mixture was stirred at room temperature for 4.5 hours and concentrated. The obtained oil was purified by silica gel column chromatography (developing solvent; chloroform:methanol=100:1) to give the object compound as a pale-yellow oil.

$[\alpha]_D$=+15.9° (c=1%, chloroform)

NMR(CDCl$_3$) δ: 0.83(m,4H), 1.00–1.13(t,3H), 1.66(m, 2H), 2.69(s,1H), 2.93(m,1H), 3.20–3.55(m,4H), 3.60(s,4H), 4.08(m,2H), 4.35(dd,1H), 4.45(dd,1H), 6.78–7.05(m,1H), 7.26(m,10H), 7.95–8.15(d,1H).

(3) Ethyl (S)-1-cyclopropyl-7-(3-(N,N-dibenzylaminomethyl)-3-fluoromethylpyrrolidin-1-yl)-6,8-difluoro-1,4-dihydro-4-oxo-3-quinolinecarboxylate Ethyl (S)-2-(4-(3-(N,N-dibenzylaminomethyl)-3-fluoromethylpyrrolidin-1-yl)-2,3,5-trifluorobenzoyl)-3-cyclopropylaminoacrylate (0.3 g) was dissolved in dry dimethylformamide (1.5 ml), and potassium carbonate (0.07 g) was added. The mixture was stirred at 50° C. for 7.5 hours. After cooling, water was added and the mixture was extracted with ethyl acetate. The extract was washed with water, dried and concentrated. The obtained oil was purified by silica gel column chromatography (developing solvent; chloroform:methanol=50:1) to give the object compound as a pale-yellow oil.

$[\alpha]_D$=1.93° (c=1%, chloroform)

NMR(CDCl$_3$) δ: 1.05(bs,2H), 1.16(d,2H), 1.40(t,3H), 1.73(m,2H), 2.70(s,1H), 3.26–3.58(m,4H), 3.63(q,4H), 3.82 (m,1H), 4.37(q,3H), 4.50(q,1H), 7.10–7.36(m,11H), 7.80(d, 1H), 8.50(s,1H).

(4) (S)-1-Cyclopropyl-7-(3-(N,N-dibenzylaminomethyl)-3-fluoromethylpyrrolidin-1-yl)-6,8-difluoro-1,4-dihydro-4-oxo-3-quinolinecarboxylic acid Ethyl (S)-1-cyclopropyl-7-(3-(N,N-dibenzylaminomethyl)-3-fluoromethylpyrrolidin-1-yl)-6,8-difluoro-1,4-dihydro-4-oxo-3-quinolinecarboxylate (7.5 g) was dissolved in ethanol (100 ml), and sodium hydroxide (0.62 g) dissolved in water (10 ml) was added. The mixture was stirred at 50° C. for 2 hours. After concentration, water was added and the pH of the solution was adjusted to 6.5 with dil. hydrochloric acid. The precipitated crystals were collected by filtration and washed with heated ethanol. The obtained crystals were recrystallized from N,N-dimethylformamide to give the object compound as pale-yellow crystals, melting point 184°–186° C.

$[\alpha]_D$=+4.8° (c=1%, chloroform)

The compound obtained is treated in the same manner as in Example 12 (2) to convert same to an 8-methoxy compound.

Example 14

(1) (S)-4-(3-(N,N-Dibenzylaminomethyl)-3-fluoromethylpyrrolidin-1-yl)- 2,3,5-trifluorobenzoic acid 2,3,4,5-Tetrafluorobenzoic acid (10 g), (R)-3-(N,N-dibenzylaminomethyl)-3-fluoromethylpyrrolidine (19.3 g) and triethylamine (5.8 g) were dissolved in dimethyl sulfoxide (25 ml), and the mixture was stirred with heating at 110° C. for 6 hours. After cooling, water was added and the mixture was extracted with ethyl acetate. The extract was washed with water, dried and concentrated. The obtained oil was purified by silica gel column chromatography (developing solvent; chloroform:methanol=30:1) to give crystals. The crystals were recrystallized from aqueous ethanol to give the object compound as white powdery crystals, melting point 140°–145° C.

$[\alpha]_D = -10.9°$ (c=1%, chloroform)

(2) (S)-4-(3-(N,N-Dibenzylaminomethyl)-3-fluoromethylpyrrolidin-1-yl)-2,3,5-trifluorobenzoyl chloride hydrochloride (S)-4-(3-(N,N-Dibenzylaminomethyl)-3-fluoromethylpyrrolidin-1-yl)-2,3,5-trifluorobenzoic acid (12.6 g) was dissolved in dry 1,2-dichloroethane (63 ml), and two drops of dry dimethylformamide were added. Thionyl chloride (2.3 ml) was added at room temperature and the mixture was refluxed for 2 hours. The reaction mixture was concentrated to give the object compound as pale-gray crystals, melting point 170°–173° C. (decomposition).

(3) Ethyl (S)-1-cyclopropyl-7-(3-(N,N-dibenzylaminomethyl)-3-fluoromethylpyrrolidin-1-yl)-6,8-difluoro-1,4-dihydro-4-oxo-3-quinolinecarboxylate (S)-4-(3-(N,N-Dibenzylaminomethyl)-3-fluoromethylpyrrolidin- 1-yl)-2,3,5-trifluorobenzoyl chloride hydrochloride (0.97 g) was dissolved in acetonitrile (8 ml). Ethyl N,N-dimethylaminoacrylate (0.27 g) and triethylamine (0.4 g) were dissolved in acetonitrile (1 ml) and dropwise added thereto with stirring at room temperature. The mixture was stirred at room temperature for 1 hour and at 50° C. for 4 hours. The reaction mixture was cooled to room temperature and cyclopropylamine (0.11 g) was added. The mixture was stirred at room temperature for 3 hours and the reaction mixture was concentrated. Water was added to the residue and the mixture was extracted with ethyl acetate. The extract was washed with water, dried and concentrated. Dry dimethylformamide (3 ml) and potassium carbonate (0.26 g) were added to the residue, and the mixture was stirred at 60° C. for 8 hours. Water was added and the mixture was extracted with ethyl acetate. The extract was washed with water, dried and concentrated. The obtained oil was purified by silica gel column chromatography (developing solvent; chloroform:methanol=30:1) to give the object compound as a pale-yellow oil.

The obtained compound is treated in the same manner as in Example 13 (4) and Example 12 (2) to convert same to an 8-methoxy compound.

ACTION AND EFFECT OF THE INVENTION

The compound (I) of the present invention wherein n is 1 retains a strong antibacterial effect against Gram-negative bacteria, as mentioned above, and additionally shows enforced and a wide range of in vitro and in vivo antibacterial effects against Gram-positive bacteria. In addition, the problematic side-effects on the central nervous system were scarcely found and the compound was low toxic. Accordingly, clinically superior utility as an antibacterial agent is expected. In particular, the compound showed a markedly enforced antibacterial effect against Gram-positive bacteria such as Staphylococcus aureus, Staphylococcus epidermidis, Streptococcus pneumoniae and Enterococcus, while retaining an antibacterial effect against Gram-negative bacteria, which was equal to or superior to that of the conventional quinolonecarboxylic acid antibacterial agents. In addition, the compound showed a strong antibacterial effect against MRSA, quinolone resistant MRSA, quinolone resistant Staphylococcus epidermidis and quinolone resistant Enterococcus, as well as against anaerobic bacteria, Chlamydia, Mycoplasma and acid-fast bacteria. Since the strong in vitro antibacterial effect against such wide range of bacteria has been proven to be consistent with the therapeutic effect in mice, the compound is expected to show extremely superior clinical effect as a therapeutic agent for various infectious diseases caused by these pathogenic bacteria. In the absence of a suitable treatment drug for multiple drug resistant MRSA which poses very serious clinical problems as a causative bacterium of nosocomial infections, or the infectious diseases caused by, from among the causative bacteria of complicated urinary tract infection, Staphylococcus epidermidis or Enterococcus having resistance to both oral cephem preparations and quinolone preparations, the clinical utility of the compound of the present invention is considered extremely high. As discussed earlier, the compounds of the present invention have antibacterial effects against an extremely broad range of pathogenic bacteria including resistant bacteria. Therefore, the compounds of the present invention are expected to scarcely cause superinfection even when administered as a therapeutic agent for bacterial infections on an extended term basis to patients who acquired immune deficiency as a result of administrations of anticancer drugs and other medicaments.

What is claimed is:

1. A 8-methoxy-quinolonecarboxylic acid derivative of the formula

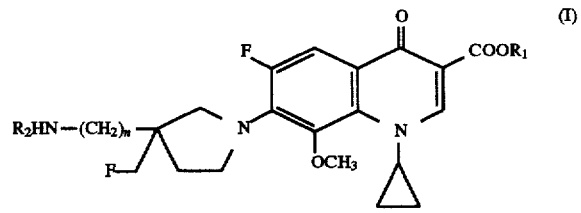

wherein $R_1$ is a hydrogen atom, a lower alkyl, a phenylalkyl or an ester residue hydrolyzable in the living body, $R_2$ is a hydrogen atom or methyl and n is an integer of 1, an optical isomer thereof, a pharmaceutically acceptable salt thereof or a hydrate thereof.

2. The 8-methoxy-quinolonecarboxylic acid derivative of claim 1, wherein $R_1$ is a hydrogen atom, an optical isomer thereof, a pharmaceutically acceptable salt thereof or a hydrate thereof.

3. The 8-methoxy-quinolonecarboxylic acid derivative of claim 1, which is a member selected from the group consisting of 7-(3-aminomethyl-3-fluoromethylpyrrolidin-1-yl)-1-cyclopropyl-6-fluoro-1,4-dihydro-8-methoxy-4-oxo-3-quinolinecarboxylic acid and 1-cyclopropyl-6-fluoro-7-(3-fluoromethyl-3-methylaminomethylpyrrolidin-1-yl)-1, 4-dihydro-8-methoxy-4-oxo-3-quinolinecarboxylic acid, an optical isomer thereof a pharmaceutically acceptable salt thereof or a hydrate thereof.

4. The 8-methoxy-quinolonecarboxylic acid derivative of claim 1, which is a member selected from the group consisting of 7-(3-aminomethyl-3-fluoromethylpyrrolidin-1-yl)-1-cyclopropyl-6-fluoro-1,4-dihydro-8-methoxy-4-oxo-3-quinolinecarboxylic acid, (R)-7-(3-aminomethyl-3- fluoromethylpyrrolidin-1-yl)-1-cyclopropyl-6-fluoro-1,4-dihydro-8-methoxy-4-oxo-3-quinolinecarboxylic acid and (S)-7-(3-aminomethyl-3-fluoromethylpyrrolidin-1-yl)-1-cyclopropyl-6-fluoro-1,4-dihydro-8-methoxy-4-oxo-3-quinolinecarboxylic acid, an optical isomer thereof, a pharmaceutically acceptable salt thereof or a hydrate thereof.

5. The 8-methoxy-quinolonecarboxylic acid derivative of claim 1, which is (S)-7-(3-aminomethyl-3-fluoromethylpyrrolidin-1-yl)-1-cyclopropyl-6-fluoro-1,4-dihydro-8-methoxy-4-oxo-3-quinolinecarboxylic acid or a pharmaceutically acceptable salt thereof.

6. A pharmaceutical composition comprising the 8-methoxy-quinolonecarboxylic acid derivative of any one of claims 1 to 5, an optical isomer thereof, a pharmaceutically acceptable salt thereof or a hydrate thereof, and a pharmaceutically acceptable carrier.

* * * * *